(12) United States Patent
Adam et al.

(10) Patent No.: US 8,841,273 B2
(45) Date of Patent: Sep. 23, 2014

(54) METHODS AND COMPOSITIONS FOR ANTI-EGFR TREATMENT

(75) Inventors: Liana Adam, Pearland, TX (US); Colin P. Dinney, Houston, TX (US); David J. McConkey, Bellaire, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/504,696

(22) PCT Filed: Oct. 28, 2010

(86) PCT No.: PCT/US2010/054514
§ 371 (c)(1),
(2), (4) Date: Jul. 17, 2012

(87) PCT Pub. No.: WO2011/059752
PCT Pub. Date: May 19, 2011

(65) Prior Publication Data
US 2013/0018088 A1    Jan. 17, 2013

Related U.S. Application Data

(60) Provisional application No. 61/255,722, filed on Oct. 28, 2009.

(51) Int. Cl.
*C12N 15/11* (2006.01)
*C12N 15/113* (2010.01)

(52) U.S. Cl.
CPC ...... *C12N 15/1138* (2013.01); *C12N 2310/141* (2013.01)
USPC .................................................. 514/44 A

(58) Field of Classification Search
USPC .................................................. 514/44 A
See application file for complete search history.

(56) References Cited

U.S. PATENT DOCUMENTS

| | | | |
|---|---|---|---|
| 2009/0131356 A1* | 5/2009 | Bader et al. | 514/44 |
| 2009/0163435 A1 | 6/2009 | Bader et al. | 514/44 R |
| 2009/0175827 A1* | 7/2009 | Byrom et al. | 424/93.2 |
| 2009/0176723 A1* | 7/2009 | Brown et al. | 514/44 |
| 2009/0192111 A1* | 7/2009 | Bader et al. | 514/44 |
| 2009/0227533 A1* | 9/2009 | Bader et al. | 514/44 |
| 2010/0310583 A1* | 12/2010 | Lieberman et al. | 424/174.1 |
| 2010/0311815 A1* | 12/2010 | Chinnaiyan et al. | 514/44 R |

OTHER PUBLICATIONS

Adam, et al., "miR-200 expression regulates epithelial-to-mesenchymal transition in bladder cancer cells and reverses resistance to epidermal growth factor receptor therapy," *Clin. Cancer Res.*, 15:5060-72, 2009.
Black, et al., "Sensitivity to epidermal growth factor receptor inhibitor requires E-cadherin expression in urothelial carcinoma cells," *Clin. Cancer Res.*, 14:1478-86, 2008.
Hurteau, et al.,"Overexpression of the microRNA hsa-miR-200c leads to reduced expression of transcription factor 8 and increased expression of E-cadherin," *Cancer Res.*, 67:7972-6, 2007.
International Search Report and Written Opinion, issued in PCT/US2010/054514, dated Mar. 29, 2011.
Korpal, et al., "The miR-200 family inhibits epithelial-mesenchymal transition and cancer cell migration by direct targeting of E-cadherin transcriptional repressors ZEB1 and ZEB2," *J. Biol. Chem.*, 283:14190-4, 2008.
McConkey, et al., "Role of epithelial-to-mesenchymal transition (EMT) in drug sensitivity and metastasis in bladder cancer," *Cancer Metastasis. Rev.*, 28:335-44, 2009.
Miyanaga, et al., "E-cadherin expression and epidermal growth factor receptor mutation status predict outcome in non-small cell lung cancer patients treated with gefitinib," *Oncol. Rep.*, 19:377-83, 2008.
Park, et al., "The miR-200 family determines the epithelial phenotype of cancer cells by targeting the E-cadherin repressors ZEB1 and ZEB2," *Genes Dev.*, 22:894-907, 2008.
Shrader, et al., "Molecular correlates of gefitinib responsiveness in human bladder cancer cells," *Mol. Cancer Ther.*, 6:277-85, 2007.
Witta, et al., "Restoring E-cadherin expression increases sensitivity to epidermal growth factor receptor inhibitors in lung cancer cell lines," *Cancer Res.*, 66:944-50, 2006.
Yauch, et al., "Epithelial versus mesenchymal phenotype determines in vitro sensitivity and predicts clinical activity of erlotinib in lung cancer patients," *Clin. Cancer Res.*, 11:8686-98, 2005.

* cited by examiner

*Primary Examiner* — Brian Whiteman
(74) *Attorney, Agent, or Firm* — Parker Highlander PLLC

(57) ABSTRACT

In some embodiments, the present invention provides methods for enhancing the sensitivity of cancer cells to anti-EGFR treatment, wherein the method comprises the introduction of a miR-200 miRNA to the cancer cells. In other embodiments, the present invention provides methods for treating cancer by exposing the cancer cells to an anti-EGFR composition after the above-mentioned enhancement step. In other embodiments, the present invention provides methods for assessing and enhancing the sensitivity of cancer cells to anti-EGFR treatment. In various other embodiments, the present invention provides compositions and expression vectors for practicing the afore-mentioned methods.

16 Claims, 7 Drawing Sheets

METHODS AND COMPOSITIONS FOR ANTI-EGFR TREATMENT

CROSS-REFERENCE TO RELATED APPLICATIONS

This application is a national phase application under 35 U.S.C. §371 of International Application No. PCT/US2010/054514 filed Oct. 28, 2010 which claims priority to U.S. Provisional Patent Application No. 61/255,722, filed Oct. 28, 2009, the entirety of which is incorporated herein by reference.

STATEMENT REGARDING FEDERALLY SPONSORED RESEARCH

This invention was made with government support under CA091846 and CA016672, both awarded by The National Institutes of Health. The government has certain rights in the invention.

FIELD OF THE INVENTION

The present invention generally pertains to the field of cancer treatment. More particularly, but not by way of limitation, the present invention pertains to the field of targeted cancer therapies, such as anti-EGFR treatment.

BACKGROUND OF THE INVENTION

The spread of cancer generally consists of numerous genetic and epigenetic factors that result in uncontrolled cellular proliferation, invasion, increased cell survival and metastatic spread. Current methods for treating cancer have limitations. For instance, though systemic chemotherapy remains palliative, it is only modestly effective. Furthermore, due to its non-specific nature, systemic chemotherapy results in numerous undesired side effects. Accordingly, targeted therapies, including inhibition of receptor tyrosine kinases, are more desirable for treating cancer. Many such therapies, such as growth factor inhibition, use algorithms that take into account target expression and validation of molecular pathways. For instance, growth factor receptors, such as the epidermal growth factor receptor (EGFR), fibroblast growth factor receptor (FGFR), or platelet-derived growth factor receptor (PDGFR) are differentially expressed by bladder cancer cell lines or tumors, making inhibitors to these molecules attractive therapeutic tools. In fact, inhibitors of the epidermal growth factor receptor (EGFR) are being evaluated for use in the treatment of urothelial cancers and other solid malignancies.

However, many cancer cell lines remain resistant to targeted therapies. For instance, many bladder cancer cell lines remain resistant to EGFR-directed therapy. Furthermore, it is at times difficult to assess or predict the resistance of cancer cell lines to targeted therapies due to the absence of ascertainable biomarkers.

Accordingly, there is currently a need to enhance the sensitivity of cancer cells to targeted therapies, such as EGFR-directed therapy (anti-EGFR treatment). There is also a need to identify biomarkers that can be used to assess the sensitivity of cancer cell lines to targeted therapies.

BRIEF SUMMARY OF THE INVENTION

In some embodiments, the present invention provides methods for enhancing the sensitivity of cancer cells to anti-EGFR treatment. Such methods generally comprise the introduction of a miR-200 miRNA to the cancer cells. In some embodiments, the miR-200 miRNA may be selected from the group consisting of miR-141, miR-200b, miR-200c, miR-205, and miR-429. Various embodiments of the present invention also pertain to methods for treating cancer. Desirably, such methods comprise the treatment of cancer cells with an anti-EGFR composition after the aforementioned enhancement step.

In other embodiments, the present invention provides methods for assessing and enhancing the sensitivity of cancer cells to anti-EGFR treatment. Such methods generally comprise the measurement of the level of a miR-200 miRNA in the cancer cells, and the introduction of a miR-200 miRNA to the cancer cells. In further embodiments, such methods may further comprise the subsequent treatment of the cancer cells with an anti-EGFR composition.

In further embodiments, the present invention provides compositions for enhancing the sensitivity of cancer cells to anti-EGFR treatment. Such compositions generally comprise an isolated miR-200 miRNA and a vector containing the miR-200 miRNA. In some embodiments, the vector may be a nanovector, such as a gold particle. In some embodiments, the vector may comprise a targeting moiety that binds to cancer cells.

In additional embodiments, the present invention provides expression vectors with an isolated polynucleotide sequence that encodes a miR-200 miRNA. In some embodiments, expression vectors may be plasmids. In other embodiments, the expression vectors may be viral vectors.

The methods, compositions, and expression vectors of the present invention can be applied to numerous cancer cells, including but not limited to bladder cancer cells, breast cancer cells, pancreatic cancer cells, lung cancer cells, and colon cancer cells. In more specific embodiments, various aspects of the present invention may be applied to bladder cancer cells, such as bladder cancer cells with a mesenchymal phenotype that are resistant to anti-EGFR treatment.

BRIEF DESCRIPTION OF THE FIGURES

For a more complete understanding of the present disclosure, and the advantages thereof, reference is now made to the following descriptions to be taken in conjunction with the accompanying Figures describing specific embodiments of the disclosure, wherein:

FIG. 1A illustrates volcano plots showing all miRNAs detected in the KU7 mesenchymal and UMUC5 epithelial cell lines (left panel). The right panel illustrates only the miRNA with significantly different expression (right panel, red dots) as opposed to non-significant levels of differential expression (right panel, blue dots). Bayesian log odds of differential expression are plotted against $\log_2$ (expression in UMUC5 divided by expression in KU7 cells).

FIG. 1B illustrates a heat map of differentially expressed miR-200 miRNAs clustered by cell type (left, low-expressed miRNAs in KU7 cells; right, high expression of the same miRNAs in UMUC5 cells).

FIGS. 1C-1G represent the quantification of miR-200 miRNAs in a panel of 9 epithelial and mesenchymal bladder cancer cell lines by real-time RT-PCR analysis. Overall, the results indicate that the miR-200 miRNAs are differentially expressed in epithelial bladder cancer cell lines that are sensitive to anti-EGFR therapy (e.g., UMUC 5, UMUC6, UMUC16, and UMUC9), but not in mesenchymal bladder cancer cell lines that are resistant to anti-EGFR therapy (e.g., KU7, UMUC 2, UMUC3, and UMUC13).

FIG. 2A illustrates data obtained after the renilla reporter plasmid harboring a miR-200c site with miR-200c precursor, or the unrelated miR-26b (control) precursor, were transiently co-transfected into KU7, UMUC3, UMUC5, and UMUC13 cells along with a firefly luciferase reporter (pGL3 control) for normalization. The data are mean±standard error of mean of separate transfections (n=6), and are shown as the ratio of Renilla activity to firefly.

FIGS. 2B-2E represent measurement by real-time RT-PCR of ZEB1, ZEB2, E-cadherin, and P-cadherin in different bladder cancer cell lines, respectively. The data are means of measurements from triplicate experiments.

FIG. 2F illustrates a heat-map of 6 differentially expressed putative targets of miR-200c in a panel of 9 bladder cancer cell lines using the Illumina gene profiling array platform.

FIG. 3A represents the measurement by real-time western blot of ERRFI-1 and E-cadherin in various bladder cancer cell lines.

FIG. 3B represents the measurement by real-time RT-PCR of mRNA relative levels of TGF-α. The data are means of measurements from triplicate experiments.

FIG. 3C represents cell proliferation measurement (DNA index) of 9 bladder cancer cell lines in the absence or presence of different concentrations of cetuximab (C225), an anti-EGFR antibody. Data are means of at least 3 triplicate experiments.

FIG. 4A illustrates phase contrast microscopy of UMUC3 cells transduced with a miR-200c containing retrovirus (UMUC3/200c) or with an empty, control retroviral construct (UMUC3-E). Scale bars represent 100 μm.

FIG. 4B illustrates the measurement of in vitro cell migration by a wound healing assay that utilized the transduced cells described in FIG. 4A. Representative pictures for same single spot are shown. The experiment was performed twice in triplicate. Scale bars represent 400 μm.

FIG. 4C represents the quantification of miR-200c in empty virus transduced (UMUC3-E) and miR-200c-transduced (UMUC3/200c) cells. The levels of miR-200c in UMUC5 cells are plotted for comparison.

FIG. 4D represents the measurement by real-time RT-PCR of the epithelial and mesenchymal markers E-cadherin, ZEB1 and ZEB2 in empty virus-transduced cells and miR-200c-transduced UMUC3 cells.

FIG. 4E illustrates confocal microscopy analyses of the UMUC3 series co-stained for ZEB1 or ZEB2 (red pixels) and nuclear DNA (green pixels). Note down-regulation of nuclear ZEB1 and ZEB2 in UMUC3 clones expressing miR-200c. The upper panel of FIG. 4F illustrates the measurement of ERRFI-1 and E-cadherin protein levels by western blot in the above-described transduced cells. Actin reprobing served as internal (loading) control. The lower panel of FIG. 4F illustrates OD relative values expressed as ratios between actin (internal control) and ERRFI-1. Note up-regulation of E-cadherin and down-regulation of ERRFI-1 protein levels upon miR-200c expression.

FIG. 5A illustrates confocal microscopy analyses of the transduced UMUC3 cells described in FIG. 4 after co-staining for ERRFI-1 (red pixels), EGFR (green pixels) and a DNA dye (blue pixels in the nucleus). Note the yellow pixels (left panel) as a result of red and green pixels co-localization.

FIG. 5B illustrates immunoblots of autophosphorylated EGFR, total EGFR, and total ERRFI-1 in cells transduced with miR-200c from the experiment described in FIG. 5A. In this experiment, actin served as the internal control.

Figure 5:
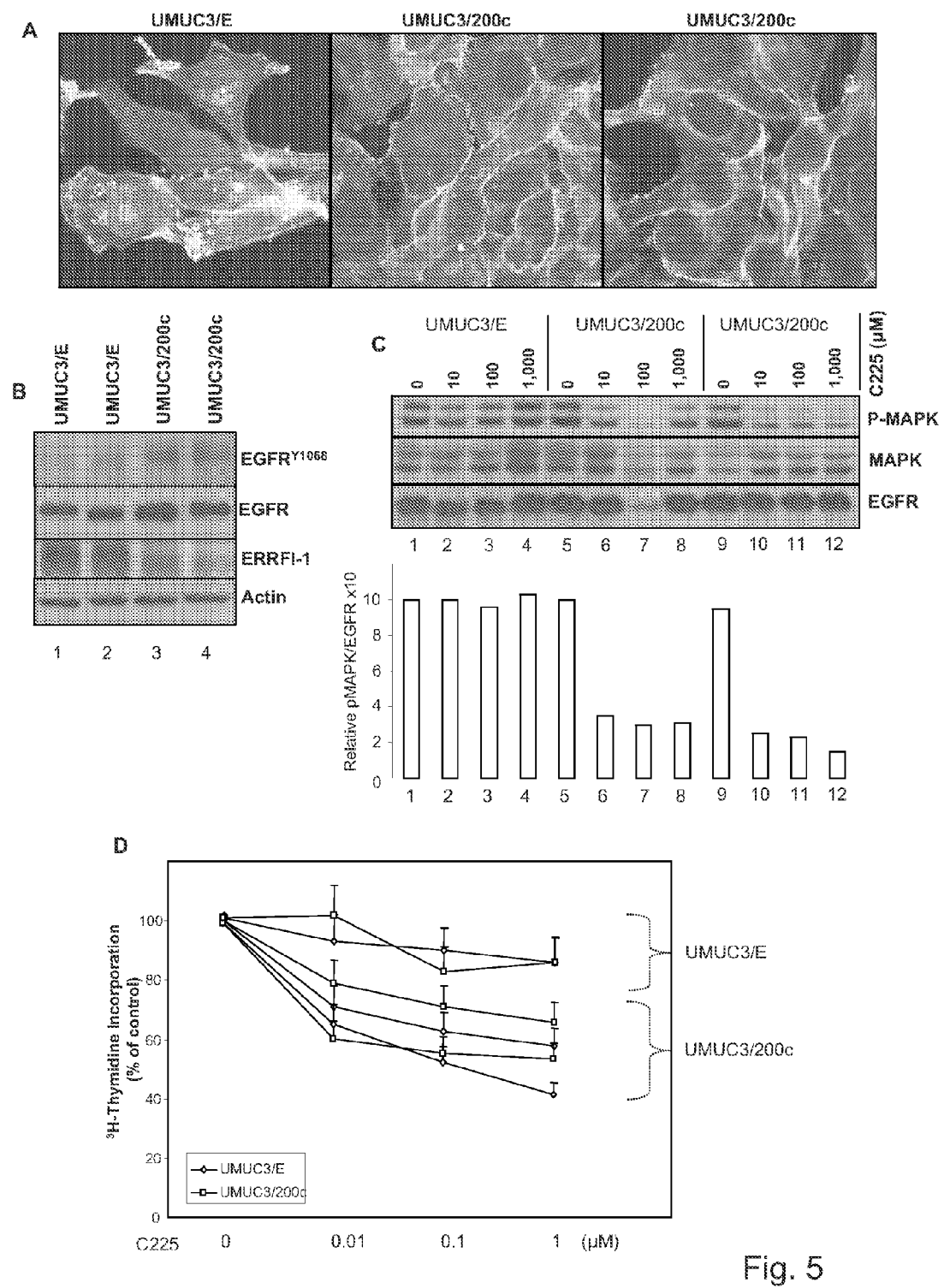
FIG. 5 illustrates that miR-200c expression reverses EGFR resistance in UMUC3 cells.

The upper panel of FIG. 5C illustrates the immunoblot of phosphorylated MAPKinase, total MAPKinase and total EGFR of the UMUC3 series. Cells were grown in 2% serum-supplemented MEM and treated with various concentrations of cetuximab (C225) for 3 hours. The lower panel of FIG. 5C illustrates the OD relative values expressed as ratios between EGFR (internal control) and pMAPKinase.

FIG. 5D illustrates cell proliferation measurement of the UMUC3 series using radioactive thymidine incorporation. Each experiment was done in at least two different triplicates.

Figure 6:
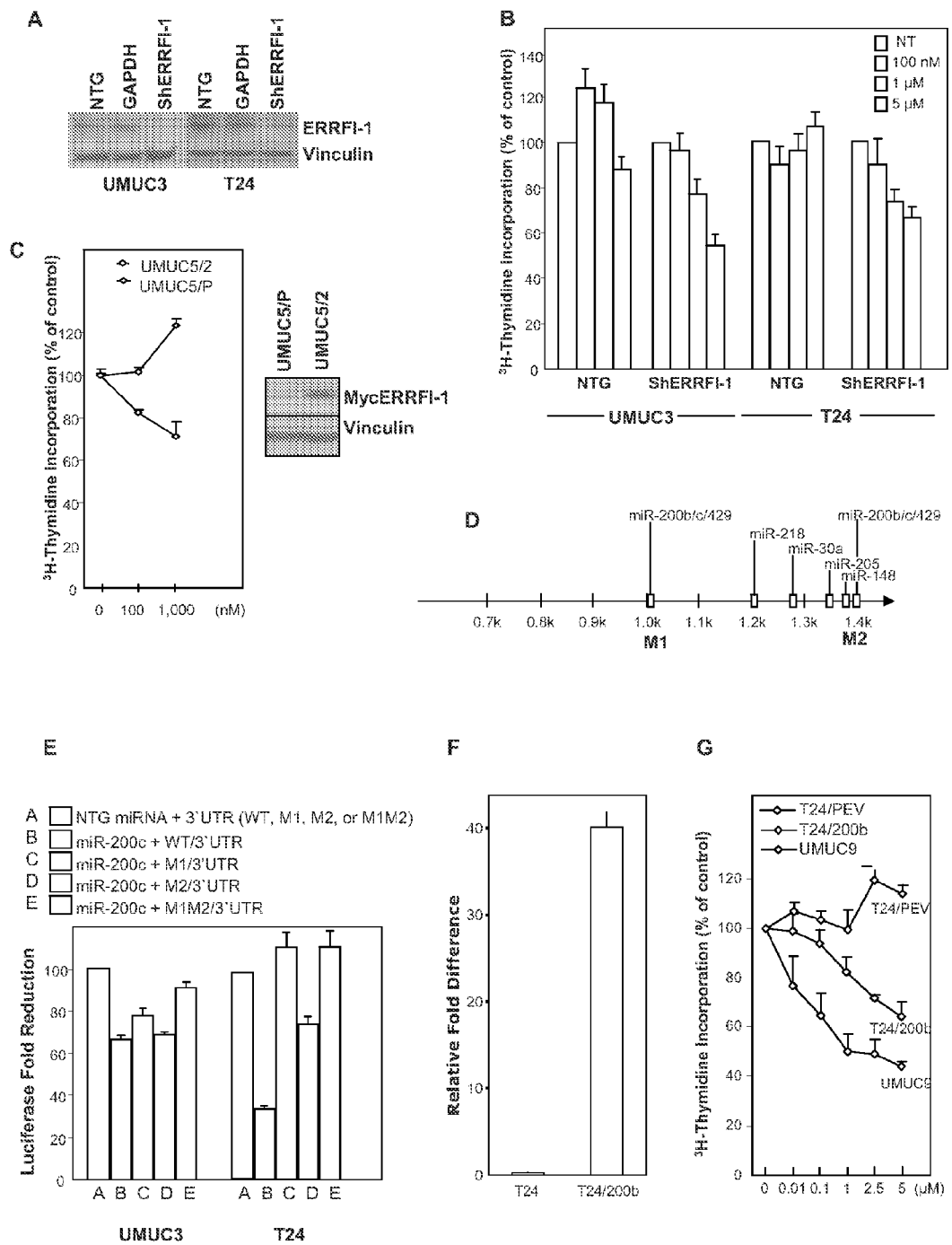

FIG. 6 illustrates that ERRFI-1 is a direct target of miR-200 and implicated in response to EGFR inhibitors.

FIG. 6A illustrates western blot measurement of ERRFI-1 protein in UMUC3 and T24 cells after transfection with a non-targeting sh construct, a GAPDH construct, or a ERRFI-1sh construct. Vinculin served as an internal control.

FIG. 6B illustrates the cell proliferation measurement of the UMUC3 and T24 series using radioactive thymidine incorporation after transfections described in the previous panel. Each experiment was done in at least two triplicates.

FIG. 6C illustrates cell proliferation measurement of the UMUC5 series using radioactive thymidine incorporation after ERRFI-1 transfection. The level of ERRFI-1 protein is shown in the right panel. Vinculin served as internal control.

FIG. 6D is a schematic representation of the 3'UTR region of ERRFI-1 displaying the miRNA potential binding sites as predicted by TargetScan. Solid boxes represent potential binding sites for miR-200b, miR-200c, and miR-429.

FIG. 6E illustrates the measurement of miR-200 repressive activity on wild-type and mutant 3'UTR/ERRFFI-1 reporters.

FIG. 6F illustrates the results of real-time RT-PCR analysis on the T24 series after miR-200b transduction using a lentiviral system. PEV, empty vector-transduced cells served as negative controls.

FIG. 6G illustrates cell proliferation measurement of the T24 series using radioactive thymidine incorporation after miR-200b lentiviral transduction and treatment with iressa (an anti-EGFR composition). Each experiment was done in at least two different triplicates. UMUC9 served as a positive control in light of its sensitivity to anti-EGFR compositions.

Figure 7:
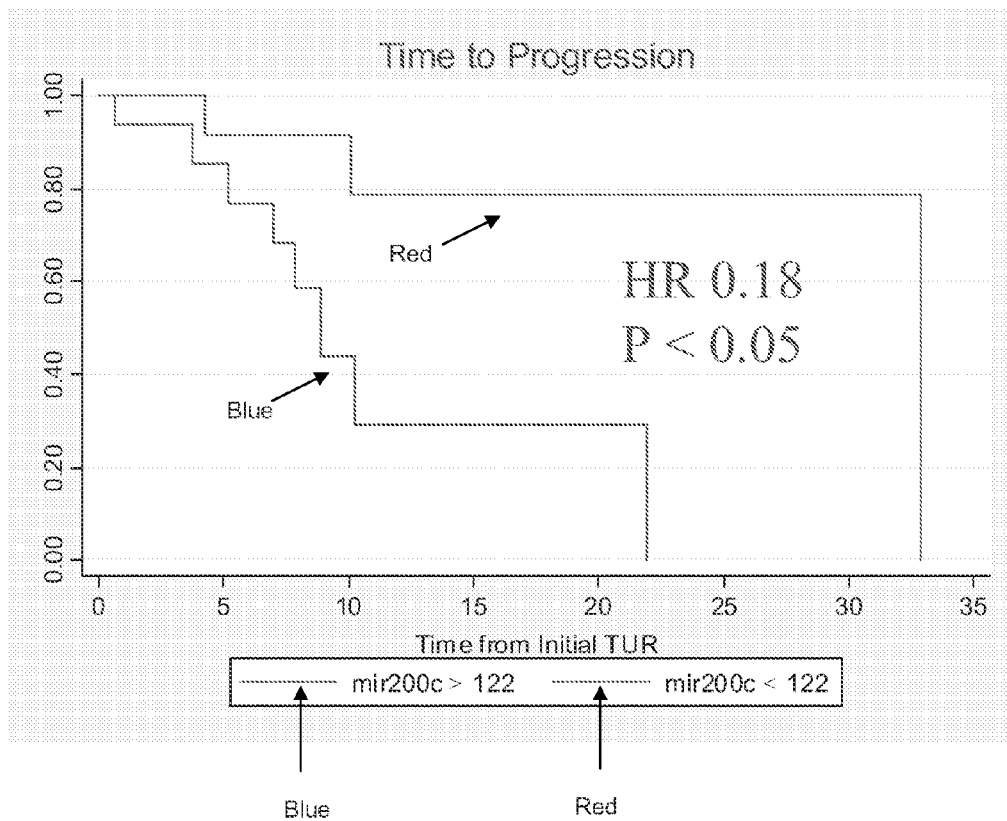

FIG. 7 illustrates the progression of urothelial cancer (UC) from the time of initial transurethral resection (TUR) in patients with miR-200C levels above and below the median level.

DETAILED DESCRIPTION OF EXEMPLARY EMBODIMENTS

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the Description or Examples below or when application of the meaning renders any construction meaningless or essentially meaningless. In cases where the construction of the term would render it meaningless or essentially meaningless, the definition should be taken from Webster's Dictionary, 3$^{rd}$ Edition.

By way of background, micro-RNAs or miRNAs are short non-coding RNAs that regulate protein production by pairing with appropriate complementary stretches in mRNAs (20, 21). Hundreds of miRNAs are encoded in the human genome, with an estimated 30% of mRNAs possessing conserved miRNA binding sites, suggesting that miRNA-based regulation is an integral component of the global gene expression program (22). The presence of diverse and often strong phenotypes, such as diseases associated with mutations or altered expression of miRNAs, suggests their importance in cell development processes and in the biology of cancers (23, 24).

For instance, and as discussed in more detail below, members of the miR-200 family of miRNAs have been shown to control the sensitivity of bladder cancer cells to anti-EGFR treatment, such as treatment with anti-EGFR antibodies and/or small molecule EGFR tyrosine kinase inhibitors. In particular, it has been shown that bladder cancer cells that show resistance to anti-EGFR treatment (EGFR-resistant cells) have relatively low levels of miR-200 miRNAs. Conversely, bladder cancer cells with sensitivity to anti-EGFR treatment (EGFR-sensitive cells) have been shown to have relatively elevated levels of miR-200 miRNAs. Furthermore, and as will be discussed in more detail below, it has been shown that the introduction of miR-200 miRNAs to bladder cancer cell lines, including EGFR-resistant cell lines, enhances the sensitivity of the cancer cells to anti-EGFR treatment.

Accordingly, some embodiments of the present invention provide methods for enhancing the sensitivity of cancer cells to anti-EGFR treatment by the introduction of one or more miR-200 miRNAs to the cancer cells. In additional embodiments, the present invention provides methods for treating cancer by exposing cancer cells to one or more anti-EGFR compositions during or after the aforementioned enhancement step. Other embodiments of the present invention provide methods for assessing and enhancing the sensitivity of cancer cells to various anti-EGFR treatments. Additional embodiments of the present invention provides compositions for enhancing the sensitivity of cancer cells to anti-EGFR treatment. As discussed in more detail below, numerous embodiments exist for various aspects of the present invention.

MiR-200 miRNAs

The methods of the present invention can utilize various miR-200 miRNA family members to enhance the sensitivity of cancer cells to anti-EGFR treatment. Non-specific examples include, but are not limited to, miR-141, miR-200b, miR-200c, miR-205, and miR-429. In some embodiments, the methods of the present invention may utilize only one miR-200 miRNA. In other embodiments, the methods of the present invention may utilize multiple miR-200 miRNAs. In more specific embodiments, the methods of the present invention may utilize miR-200c to enhance the sensitivity of cancer cells to anti-EGFR treatment. However, a person of ordinary skill in the art can envision the use of other miR-200 family members with various embodiments of the present invention that have not been listed in this disclosure. In some embodiments, such miR-200 family members may also include miR-200 miRNAs that have not yet been discovered or identified.

Introduction of miR-200 miRNAs to Cancer Cells

The present invention can also utilize various methods to introduce one or more miR-200 miRNAs to cancer cells. For instance, in some embodiments, one or more miR-200 miRNAs may be introduced to the cancer cells by transfecting the cancer cells with the miR-200 miRNAs. In more specific embodiments, the transfection may comprise the use of a nanovector, such as a gold particle, to deliver one or more miR-200 miRNAs to the cells. In additional embodiments, miR-200 miRNAs may be introduced to cancer cells by lipofection, such as by the use of Invitrogen's Lipofectamine™ Transfection Reagents in one example. Other transfection methods well known by persons of ordinary skill in the art can also be utilized in other embodiments to introduce miR-200 miRNAs to cancer cells.

In some embodiments, miR-200 miRNAs are introduced to cancer cells by a targeted delivery method. Such methods generally comprise the use of a targeting moiety that binds to one or more cancer cells. For instance, in various embodiments, the targeting moiety can be a small molecule, an aptamer, a dendrimer, and/or an antibody. In more specific embodiments, the targeting moiety is a monoclonal antibody that binds to a receptor that is over-expressed on cancer cells. Other suitable targeting moieties can also be envisioned by persons of ordinary skill in the art.

In more specific embodiments, the targeted delivery method may consist of the delivery of one or more miR-200 miRNAs to cancer cells by the use of a nanovector that has one or more targeting moieties (as described above). Other suitable targeted delivery methods can also be envisioned by persons of ordinary skill in the art.

In other embodiments, one or more miR-200 miRNAs may be introduced to cancer cells by transfecting the cancer cells with an expression vector that encodes a nucleotide sequence for one or more miR-200 microRNAs, such as miR-200c. Thereafter, the cells may express the encoded miR-200 in the expression vector by transcription. In some embodiments, the expression vector may be a plasmid. In various embodiments, the expression vectors may be introduced to the cancer cells by conventional methods, such as by lipofection (as previously described), electroporation, or other methods well-known by persons of ordinary skill in the art.

In additional embodiments, miR-200 miRNAs may be introduced to the cancer cells by the transduction of the cancer cells with a viral vector that encodes a nucleotide sequence for one or more miR-200 microRNAs. In some embodiments, the viral vector may be a retrovirus, such as a lentivirus. In additional embodiments, the viral vector may be an adenovirus. In further embodiments, other viral vectors well-known by persons of ordinary skill in the art may be used to introduce miR-200 miRNAs to cancer cells.

Without being bound by theory, and as it will be discussed in more detail below, the introduction of one or more miR-200 miRNAs to the cancer cells enhances the sensitivity of the cancer cells to anti-EGFR treatment. In some embodiments, such enhancement may be characterized by an increase in the effectiveness of a particular anti-EGFR treatment in the cancer cells (when compared with the effectiveness of the anti-EGFR treatment in cancer cells without the introduced miR-200 miRNAs). In some embodiments, the increase in the effectiveness of an anti-EGFR treatment may be characterized by the inhibition of cancer cell growth, as determined by various assays (e.g., without limitation, $3^H$-thymidine incorporation assays, MTT cell proliferation assays, Gel Microdrop (GMD) Growth Assays, colorometric growth assays, etc.). In further embodiments, the enhancement of the sensitivity of the cancer cells to anti-EGFR treatment may be characterized by other methods well-known by persons of ordinary skill in the art.

In various embodiments, the enhancement of the sensitivity of cancer cells to anti-EGFR treatment may also be characterized by changes in cell morphology and/or gene expression. For instance, in some embodiments, the enhancement of the sensitivity of cancer cells to anti-EGFR treatment may be characterized by the transformation of the cancer cells, such as bladder cancer cells, from mesenchymal cells to epithelial cells. In some embodiments, the enhancement may also be characterized by the up-regulation of the expression of various proteins in the cancer cells, such as E-cadherin and ERRFI-1. Similarly, in some embodiments, the enhancement of the sensitivity of the cancer cells to anti-EGFR treatment may also be characterized by the down-regulation of the expression of various genes in the cancer cells, such as ZEB 1 and ZEB 2. The aforementioned proteins will be described in more detail below.

Anti-EGFR Treatments

A person of ordinary skill in the art will also recognize that the methods of the present invention may be used to enhance the sensitivity of cancer cells to various anti-EGFR treatments. A person of ordinary skill in the art will also recognize that various embodiments of the present invention may utilize numerous anti-EGFR treatments to treat cancer. In various embodiments, the anti-EGFR treatment may occur before, during and/or after the aforementioned enhancement steps. In other embodiments, the anti-EGFR treatment may occur before, during and after the enhancement step.

In some embodiments, the anti-EGFR treatment may comprise or refer to the treatment of cancer cells with one or more anti-EGFR antibodies. Such antibodies may include, without limitation, cetuximab (C225) and panitumumab.

Likewise, in some embodiments, the anti-EGFR treatment may refer to or comprise the treatment of cancer cells with one or more small molecule EGFR tyrosine kinase inhibitors. In some embodiments, such inhibitors may include, without limitation, iressa, erlotinib (Tarceva), gefitinib, sorafenib, sunitinib, and lapatinib.

In further embodiments, the anti-EGFR treatment may refer to or comprise the simultaneous treatment of cancer cells with one or more small molecule EGFR tyrosine kinase inhibitors, and one or more anti-EGFR antibodies. In additional embodiments, the anti-EGFR treatment may refer to or comprise numerous steps, such as a treatment regimen. Furthermore, a person of ordinary skill in the art will recognize that the methods of the present may refer to or utilize numerous other anti-EGFR treatments, including anti-EGFR treatments that have not yet been identified, developed or discovered.

Cancer Cells

A person of ordinary skill in the art will also recognize that the methods of the present invention may be applied to various cancer cells. For instance, in various embodiments, the methods of the present invention may be applied to human cancer cells. In other embodiments, the methods of the present invention may be applied to mouse cancer cells. In some embodiments, non-limiting examples of cancer cells that may be treated by the methods of the present invention may include, without limitation, bladder cancer cells, breast cancer cells, pancreatic cancer cells, lung cancer cells, and colon cancer cells. In more specific embodiments, the methods of the present invention may be applied to bladder cancer cells that display a "mesenchymal phenotype" (mesenchymal cells), such as UMUC2, UMUC3, UMUC13, and/or KU7 cells. As it will be discussed in more detail below, such mesenchymal bladder cancer cells have shown resistance to anti-EGFR treatment. Furthermore, it has been shown that such resistance can be reversed by the introduction of one or more miR-200 microRNAs to the cancer cells.

Assessing the Sensitivity of Cancer Cells to Anti-EGFR Treatment

In addition to providing methods for treating cancer and methods for enhancing the sensitivity of cancer cells to anti-EGFR treatment, the present invention also provides methods for assessing the sensitivity of cancer cells to various anti-EGFR treatments. Such methods generally comprise a measurement of a level of one or more miR-200 miRNAs in the cancer cells. In such embodiments, the measured level of a miR-200 miRNA may then be directly correlated to the sensitivity of the cancer cells to anti-EGFR treatment.

As discussed in more detail below, observations that miR-200 levels in bladder cancer cells are directly correlated to the sensitivity of the cells to anti-EGFR treatment provides support for the above-mentioned embodiments of the present invention. Furthermore, and as will be discussed in more detail below, increased miR-200 expression patterns were observed in EGFR-sensitive cells after anti-EGFR treatment. However, EGFR-resistant cells did not show increased expression patterns after the same anti-EGFR treatments. Accordingly, in other embodiments, the present invention can provide methods for assessing the sensitivity of cancer cells to anti-EGFR treatment by measuring the level of one or more miR-200 miRNAs in the cancer cells after anti-EGFR treatment. The measured level of miR-200 miRNAs may then be directly correlated to the sensitivity of the cancer cells to anti-EGFR treatment.

A person of ordinary skill in the art will also recognize that various methods may be used to measure miR-200 microRNA levels in a cancer cell. For instance, in some embodiments, the level of one or more miR-200 microRNAs may be measured by real-time RT-PCR analysis of the RNA in the cancer cells. In some embodiments, the measurement may also comprise a measurement of miR-200 microRNA levels in urine or serum samples of a patient. A person of ordinary skill in the art will also recognize additional methods for measuring miR-200 microRNA levels, including methods that have not yet been developed.

Compositions and Expression Vectors

In further embodiments, the present invention provides compositions for enhancing the sensitivity of cancer cells to anti-EGFR treatment. Such compositions may generally comprise one or more isolated miR-200 miRNAs, and a vector for introducing the miR-200 miRNAs to the cancer cells. In some embodiments, the vector may be a nanovector, such as a gold particle. In some embodiments, the miR-200 miRNAs may be miR-200c. In further embodiments, the vector may comprise one or more targeting moieties (as previously described).

In additional embodiments, the present invention may also provide an expression vector, such as a plasmid or a viral vector (as previously discussed), that comprises an isolated polynucleotide sequence that encodes one or more miR-200 miRNAs. For instance, in some embodiments, the isolated polynucleotide sequence may express miR-200c.

Applications

A person of ordinary skill in the art will also recognize that the methods, compositions and expression vectors of the present invention may be used in various setting and for numerous purposes. For instance, in some embodiments, the methods, compositions, and expression vectors of the present invention may be used in vitro, such as for basic research or validating a targeted therapy regimen. In other embodiments, the methods, compositions and expression vectors of the present invention may be used in vivo, such as in a live animal or a human being, to treat cancer. For instance, in a more specific embodiment, one or more miR-200 miRNAs may be intravenously administered to a human patient for delivery to a desired tumor site by known methods, such as the above-described transfection and/or transduction methods. Thereafter, the human patient may be treated with one or more anti-EGFR compositions, such as the above-discussed compositions.

From the above disclosure, a person of ordinary skill in the art will recognize that the present invention has numerous embodiments and applications. Reference will now be made to more specific embodiments of the present invention and experimental results that provide support for such embodiments. However, Applicants note that the disclosure below is for exemplary purposes only and is not intended to limit the scope of the present invention in any way.

Assessing and Enhancing the Sensitivity of Bladder Cancer Cells to Anti-EGFR Treatment In a specific embodiment, the methods, expression vectors and compositions of the present invention may be used to assess and enhance the sensitivity of bladder cancer cells to anti-EGFR treatment. By way of background, bladder cancer is a common malignancy characterized by frequent recurrences and a poor clinical outcome when tumors progress to invasive disease. Growth factor receptors, such as the epidermal growth factor receptors (EGFR), fibroblast growth factor receptors (FGFR), and platelet-derived growth factor receptors (PDGFR) are differentially expressed by bladder cancer cell lines or tumors, making inhibitors to these molecules attractive therapeutic tools (3-5). Without being bound by theory, debate is ongoing as to whether EGFR expression or mutation in the tyrosine kinase domain correlates well with response to EGFR blockade by tyrosine kinase inhibitors (TKIs) and to survival. In previous studies, it was demonstrated that mutations in the EGFR protein or gene amplifications were not as frequent in bladder cancer as in other cancers, such as lung cancer (6, 7), suggesting that other predictors remain to be identified. Very recently, several groups reported that sensitivity to EGFR-directed treatment is associated with expression of E-cadherin and other properties of a typical "epithelial" tumor phenotype (8-13).

By way of further background, a phenomenon known as epithelial to mesenchyme transition (EMT) has been implicated as having a role in tumor invasion/migration and metastasis of many forms of cancers, including bladder cancer (14). Loss of E-cadherin expression is a hallmark of the EMT process, which may be required for enhanced tumor-cell motility. During EMT, down-regulation of E-cadherin allows epithelial cells to undergo changes in cell morphology and motility so that they adopt mesenchymal characteristics. Expression of E-cadherin is controlled by several transcriptional repressors, including Twist, Snail1, Snail2/Slug, E47, ZEB1/TCF8, and ZEB2/SIP1, which bind to E-boxes in the E-cadherin promoter (15).

Furthermore, recent studies have demonstrated that ZEB1 and ZEB2 are direct targets of miRNAs from the miR-200 family in human breast cancer cells (MDA-MB231), canine kidney cells (MDCK), murine models and a NCI-60 panel of cell lines (16-19). In particular, many studies have identified a new role for miR-200c, miR-141, miR-200b, and miR-205, all members of the miR-200 family of miRNAs, in EMT through the direct regulation of ZEB1 and ZEB2 (16-17 and 19). Studies also showed that ectopic expression of these miRNAs leads to re-expression of E-cadherin and epithelial phenotypes in NMuMG murine mammary model that have undergone EMT upon TGF-β stimulation (18). The same results have been observed in mesenchymal MDAMB231 cells (16).

To determine whether one or more miR-200 family members could be used as biomarkers to identify bladder cancer cells (BCC) that may be sensitive to anti-EGFR treatment, and to determine whether the introduction of one or more miR-200 family members to the bladder cancer cells could help enhance their sensitivity to anti-EGFR treatment, Applicants performed various experiments. As set forth in more detail below, the results of such experiments indicate that one or more miR-200 family members can be used as biomarkers to assess the sensitivity of bladder cancer cells to anti-EGFR treatment. The results also indicate that the introduction of one or more miR-200 family members to the bladder cancer cells can help enhance their sensitivity to anti-EGFR treatment. The experimental details for such results will now be discussed in more detail.

MiR-200 miRNAs are Differentially Expressed in "Epithelial", EGFR-Sensitive Bladder Cancer Cells.

Figure 1:
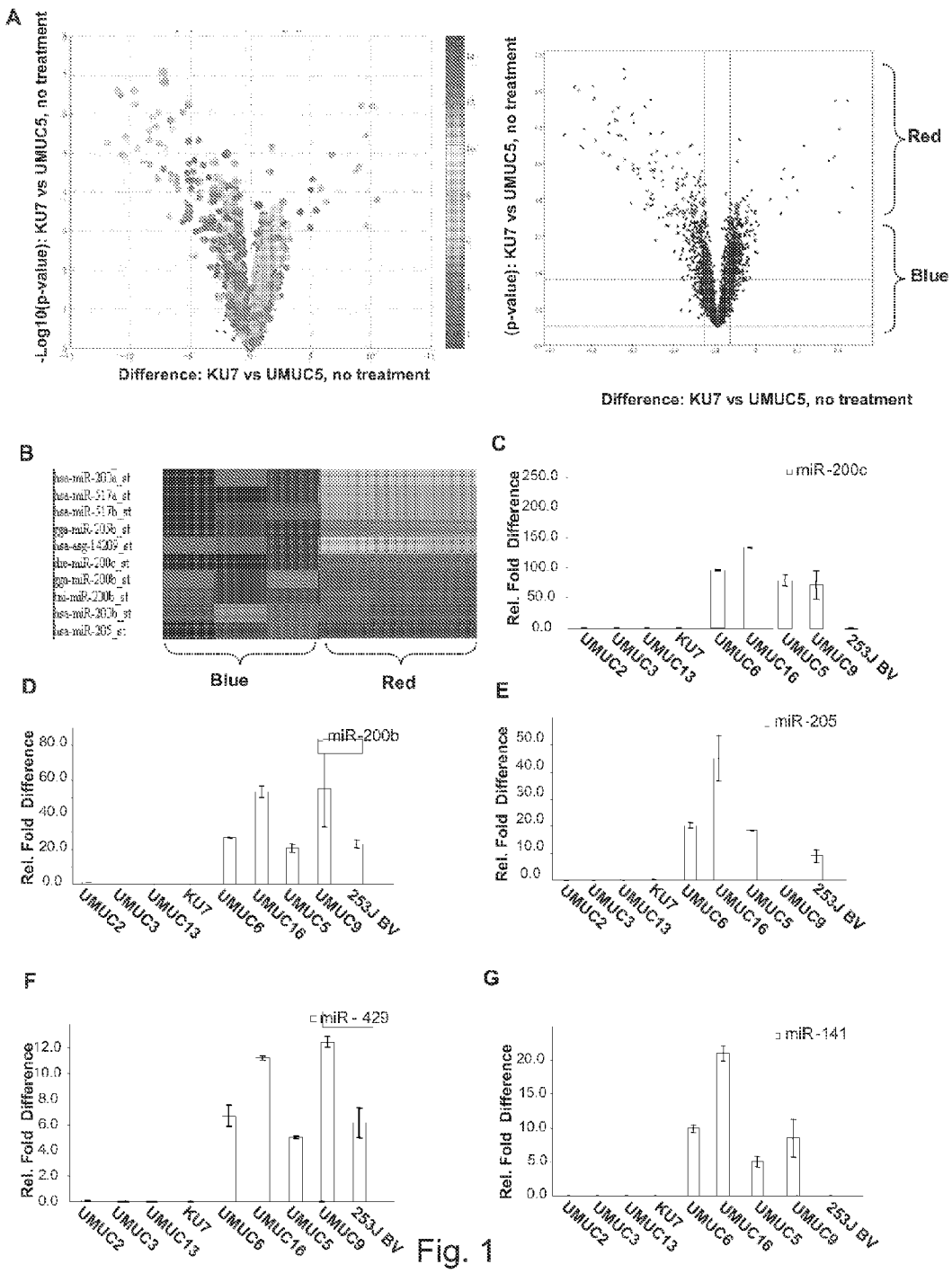
FIG. 1 illustrates the identification of miRNAs that are differentially expressed in epithelial versus mesenchymal bladder cancer cell lines.

To identify miRNAs that might be important for regulating E-cadherin expression and EGFR-sensitivity (i.e., sensitivity to anti-EGFR treatment), we compared global miRNA expression patterns in 2 bladder cancer cell lines: (1) an EGFR-sensitive, E-cadherin-positive cell line (UMUC5); and (2) an EGFR-resistant, E-cadherin negative, and vimentin-positive cell line (KU7). We used miRNA array analysis that contained a dataset composed of all known miRNAs biologically demonstrated or predicted through bioinformatics (Assuragen, MiRInform, December 2007). Triplicate samples of untreated and cetuximab (C225)-treated UMUC5 and KU7 cells were analyzed using this platform. A diagram demonstrating the total number of miRNA species expressed by the 2 cells without treatment is shown in FIG. 1A (left panel). All miRNAs were then ranked according to the differences in expression between the untreated epithelial and mesenchymal cells with a cut-off of a two-fold difference between the 3 replicate samples of the cells (FIG. 1A, right panel, red dots).

Next, we performed a cluster analysis in which we grouped the known (validated) and the predicted miRNAs by their level of differential expression. One example of such a cluster is shown in FIG. 1B. Six miR-200 miRNAs were then selectively expressed at very high levels in the epithelial UMUC5 cells compared to mesenchymal KU7 cells. These miRNAs were miR-200a, miR-141, miR-200b, miR-200c, miR-429, and miR-205.

We then used real-time RT PCR analysis to evaluate the expression of the miR-200 family of miRNAs in a panel of 9 bladder cancer cells that display varying sensitivities to anti-EGFR treatment. In particular, the panel contained 4 EGFR-sensitive epithelial cell lines (UMUC6, UMUC9, UMUC16, UMUC5 and UMUC6), 5 EGFR-resistant mesenchymal cell lines (UMUC2, T24, UMUC3, UMUC13, and KU7), and 1 cell line that contained markers of both phenotypes (253J B-V). Importantly, the latter cell line was derived from 253J cells through 5 cycles of in vivo selection as previously described (26) with the goal of producing a more invasive phenotype. Accordingly, the resultant 253J B-V cells were highly invasive in vitro and in vivo. In particular, the epithelial characteristics of the mother cell were lost in the 253J B-V cells (12).

As illustrated in FIGS. 1C-1G, we observed increased expression of miR-200c, miR-200b, miR-205, miR-429, and miR-141 in all the EGFR-sensitive "epithelial" cells, including the UMUC5 cells. In contrast, we observed that the miR-200 expression levels were very low in the EGFR-resistant "mesenchymal" cells, including the KU7 cells. The 253J BV cells, which express low levels of E-cadherin and some vimentin (12), and are considered to be part of the EGFR-sensitive group, displayed co-expression of 3 of the miR-200 family members (FIG. 1D-G). Overall, the results suggest that the miR-200 family members are important regulators of EMT and anti-EGFR sensitivity in bladder cancer cells. The results also indicate that the miR-200 family members can be used as biomarkers to assess the sensitivity of bladder cancer cells to anti-EGFR treatment.

In addition, we observed that miR-141 was co-expressed with miR-205 in the EGFR-sensitive UMUC5, UMUC6, UMUC9, and UMUC16 cells. However, the UMUC9 cell line lacked miR-205, whereas 253J BV cells lacked miR-141 (FIGS. 1E and 1G).

MiR-200c is Up-Regulated in EGFR-Sensitive Cells in Response to Anti-EGFR Treatment, but not in EGFR-Resistant Cells.

Next, we compared miRNA expression patterns in UMUC5 and KU7 cells that were incubated with or without the anti-EGFR composition C225. The results revealed that miR-200c was the only miRNA species induced substantially in the EGFR-sensitive UMUC5 cells in response to C225 treatment. However, no miRNA species, known or predicted, was modulated substantially by the EGFR-resistant KU7 cells after incubation with C225 (data not shown). The abovementioned observations were corroborated by Applicants' personal observations that C225 treatment induced up-regulation of E-cadherin in EGFR-sensitive UMUC5 cells.

Overall, the above results and observations indicate that miR-200c is a preferred candidate to use in a study of the relationship between the EMT and the sensitivity of bladder cancer cells to anti-EGFR treatment. The results also indicate that anti-EGFR treatment may up-regulate the expression of miR-200 miRNAs in EGFR-sensitive bladder cancer cells, but not in EGFR-resistant cells.

Figure 2:
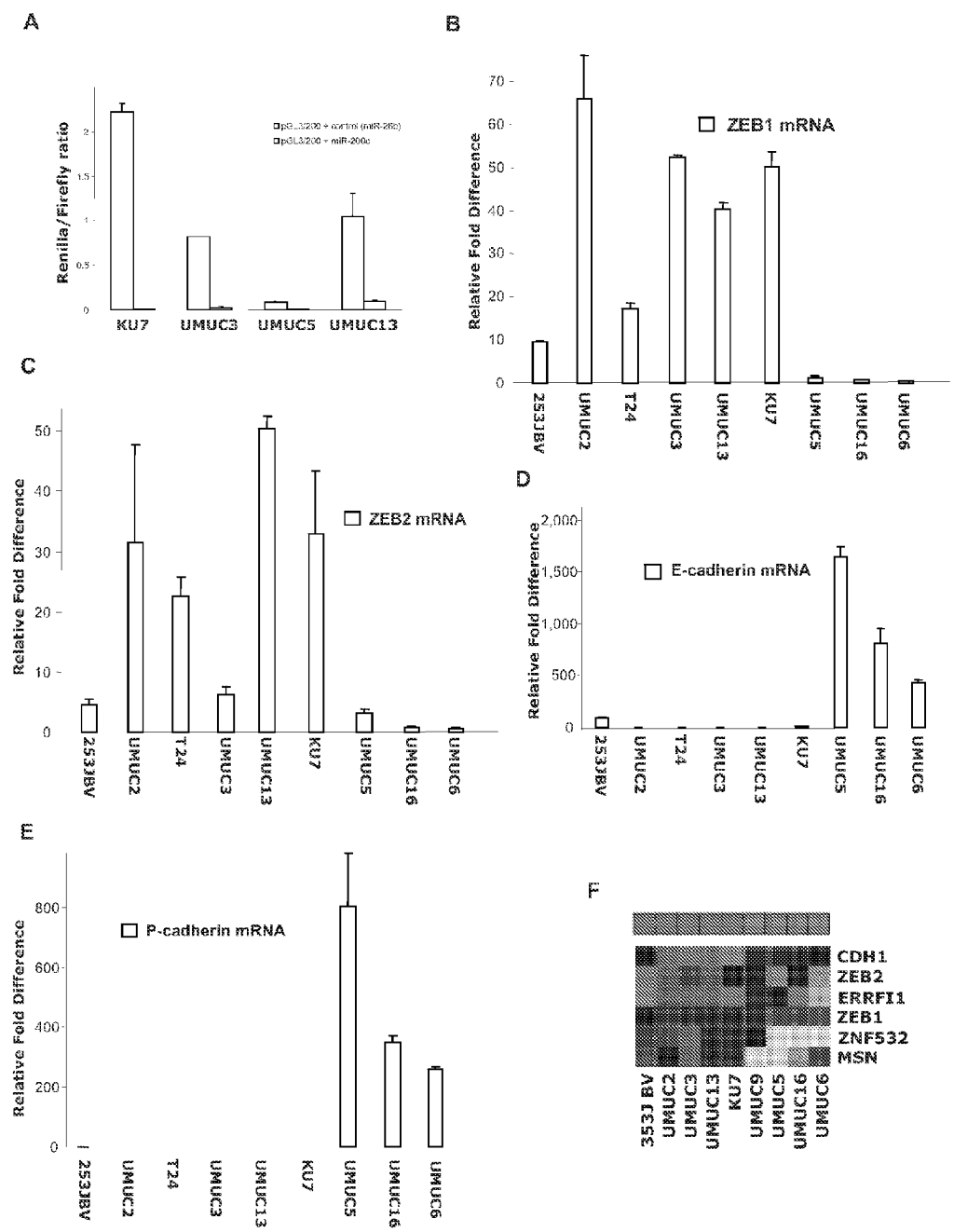
FIG. 2 represents the identification of miR-200 direct targets in a panel of bladder cancer cell lines.

Because miR-200c, miR-200b, and miR-429 target the same sequences in their target mRNAs, and because miR-200c seemed to be associated with the EGFR-sensitive epithelial phenotype, we next decided to use a luciferase-based reporter system to measure the functionality of miR-200 family members in the above-described panel of bladder cancer cell lines. In particular, a reporter plasmid harboring a miR-200c site with a miR-200c precursor, or an unrelated miR-26b (control) precursor, were transiently co-transfected into KU7, UMUC3, UMUC5, and UMUC13 cells along with a firefly luciferase reporter (pGL3 control) for normalization. As shown in FIG. 2A, the EGFR-sensitive UMUC5 epithelial cell line showed low baseline luciferase activity as opposed to the EGFR-resistant mesenchymal cell lines (KU7, UMUC3, and UMUC13). Such results demonstrated that miR-200 family members expressed by E-cadherin-positive EGFR-sensitive cells were likely to be functional.

ZEB1, ZEB2, and ERRFI-1 are Inversely Correlated with miR-200 Expression.

Further real-time RT-PCR analysis in the same panel of bladder cancer cell lines revealed that the expression of miR-200 family members was inversely correlated with the expression of ZEB1 and ZEB2 (FIGS. 2B and 2C, respectively). In addition, Applicants also observed that the expression of E-cadherin suppressors ZEB1 and ZEB2 were inversely correlated with the E-cadherin expression (FIG. 2D). Such results suggest that the EGFR-sensitive epithelial phenotype of bladder cancer cells may also be regulated by miR-200 family members as it has been recently described in breast cancer cells (16), NCI-60 cell lines (19), colon cancer cells (17) and a murine model of EMT (18).

Furthermore, we also looked for other classical cadherins that are involved in homotypic interactions and found that P-cadherin was also associated with the expression of miR-NAs of the miR-200 family (FIG. 2E). However, P-cadherin did not correlate with EGFR sensitivity because it was not expressed by 253J-BV (FIG. 2D compared to FIG. 2E).

Figure 3:
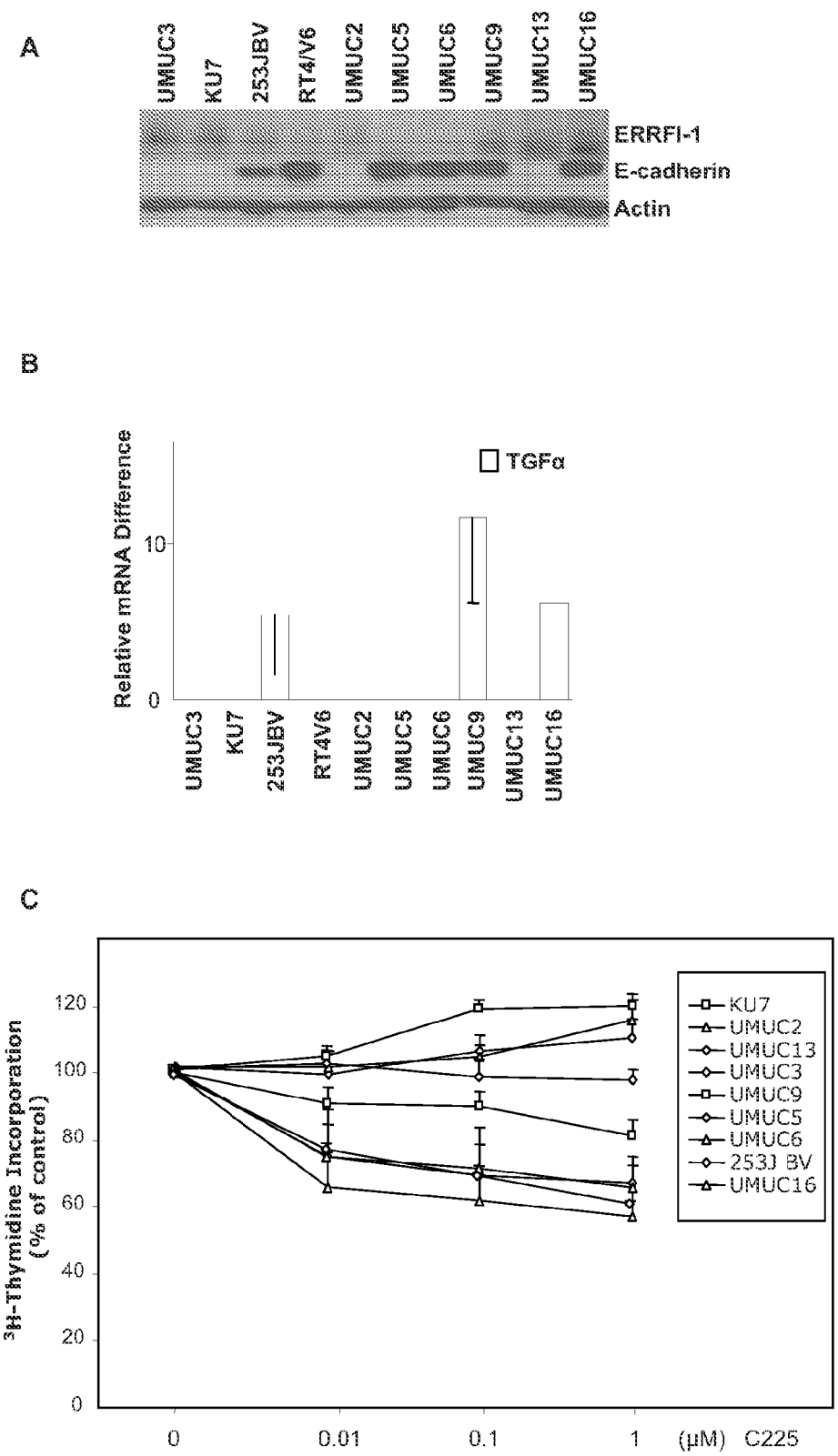
FIG. 3 illustrates the relation between the differentially expressed ERRFI-1 and TGF-α and cell sensitivity to anti-EGFR treatment.

Next, we utilized the TargetScan and PictarVert databases for potential direct targets of miR-200b, miR-200c, and miR-429 that would be associated with an EGFR-sensitive phenotype. Several targets were identified according to their ranking in terms of content of conserved miR-200 sites and their expression pattern in our panel of bladder cancer cell lines as a result of gene expression profiling of the 9 cell lines. This list included ZEB1, ZEB2, ERRFI-1, MSN (a modulator of the cytoskeleton), and an unknown Zn finger transcription factor (ZNF532). A heat map showing the relative differences between the cell lines with respect to these potential miR-200 direct targets is shown in FIG. 2F. Further scrutiny for known direct modulators of EGFR-related signaling eliminated all of the targets except ERRFI-1. In addition, real-time RT-PCR analysis revealed that ERRFI-1 mRNA levels were very low in 3 of 5 EGFR-sensitive epithelial cell lines and high in all 3 EGFR-resistant mesenchymal cell lines (FIG. 3A). Such results suggest that ERRFI-1 is a good candidate target of the miR-200 miRNAs. The results also indicate that the higher baseline expression of ERRFI-1 may be a component of anti-EGFR-resistance.

Analysis of the 3'UTR region of ERRFI-1 and ZEB1/ZEB2 revealed that, although ZEB1 and ZEB2 displayed at least 5 potential binding sites for the miR-200 family members (miR-200a, miR-200b, miR-200c, miR-429, miR-141, and miR-205), ERRFI-1 displayed 2 such conserved sites (http:TargetScan.org). ERRFI-1 also displayed an additional miRNA conserved site for miR-148 and miR-152, which were not found in either ZEB1 or ZEB2 3'UTRs. We then analyzed the expression pattern of miR-148 in the panel of bladder cancer cell lines and found no correlation with an epithelial or a mesenchymal phenotype, which underscored its role as a primary ERRFI-1 regulator (data not shown).

Because a property of ERRFI-1 is its ability to bind more tightly to activated EGFR than to the un-ligated receptor, we next determined which EGFR ligands are expressed by our cell lines. As shown in FIG. 3B, gene expression array analysis revealed that three of the E-cadherin-positive and EGFR-sensitive cell lines (253JBV, UMUC16, and UMUC9) also expressed TGF-α. However, as also shown in FIG. 3B, none of the mesenchymal EGFR-resistant cell lines expressed this gene. In addition, these "autocrine-positive" and E-cadherin positive cells displayed slightly higher levels of the ERRFI-1 protein (FIG. 3A), suggesting that the "feed-back" mechanism of ligand-induced ERRFI-1 up-regulation is present in these cells, as previously described (27). Importantly, UMUC5 and UMUC6, each of which are E-cadherin positive and TGF-α negative, had almost undetectable levels of ERRFI-1 protein (FIGS. 3A and 3B).

C225 Inhibited Proliferation of EGFR-Sensitive Cells, but not EGFR-Resistant Cells Next, we evaluated the cell growth inhibition of the above-mentioned bladder cancer cell lines by C225 (cetuximab) based on a $^3$H-thymidine incorporation assay. As shown in FIG. 3C, the results revealed that cetuximab inhibited cell growth in EGFR-sensitive cells, but not in EGFR-resistant cells. In particular, the results revealed that KU7, UMUC2, UMUC13, and UMUC3 (EGFR-resistant, E-cadherin negative cells that were high expressers of ERRFI-1), were resistant to up to 1 μM of C225. On the other hand, cell proliferation was inhibited by up to 40% by 1 μM of C225 in UMUC9, 253J BV, and UMUC16 (EGFR-sensitive, moderate ERRFI-1 expressers and high TGF-α expressers), as well as in UMUC5 and UMUC6 (EGFR-sensitive without detectable expression of ERRFI-1 or TGF-α).

Applicants further note that the above assays were done in EGF-unstimulated or "baseline" growth conditions. In particular, the assays were performed in the presence of Dulbecco's MEM supplemented with 2% fetal calf serum, which reflects non-optimal conditions for the inhibitory effects of C225.

MiR-200c Expression Induced a Mesenchymal to Epithelial Transition (MET) Phenotype in EGFR-Resistant Cells.

Figure 4:
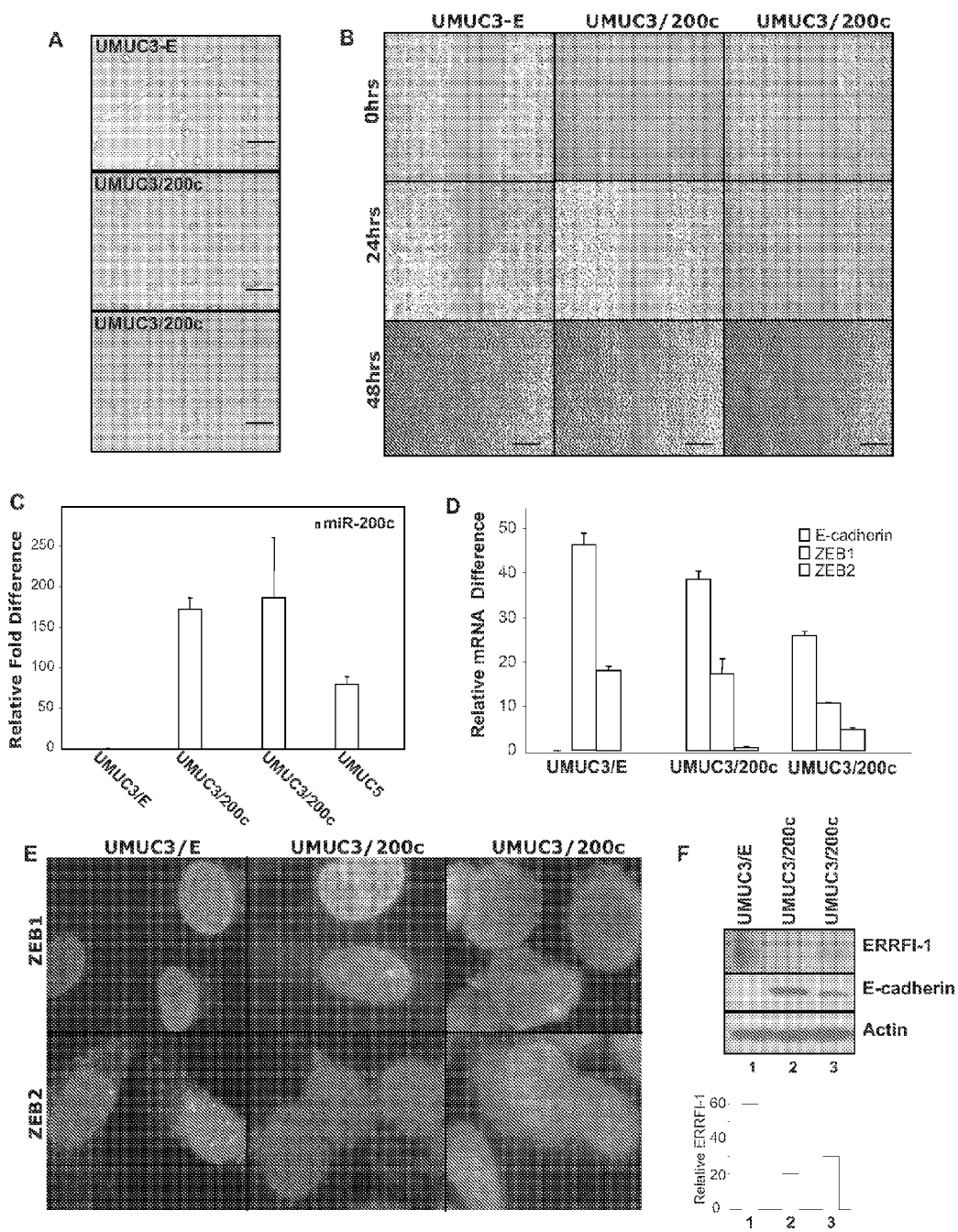
FIG. 4 illustrates that the miR-200c expression induces an epithelial to mesenchymal transition (EMT) phenotype in the UMUC3 mesenchymal bladder cancer cell line.

To more directly define the role of miR-200c in enhancing or maintaining EGFR-sensitivity in bladder cancer cells, we stably transduced the EGFR-resistant mesenchymal UMUC3 cells with a retroviral vector containing the miR-200c precursor in accordance with previously-used methods (16). As shown in FIG. 4A, stable expression of miR-200c in fibroblast-like mesenchymal UMUC3 cells resulted in morphological changes suggestive of epithelial differentiation. In particular, it was observed that the cells grew in a more compact fashion and displayed cobblestone-like cell morphologies. Furthermore, as shown in FIG. 4B, these changes were associated with a reduced invasive phenotype as measured by in vitro wound-healing assays, where the miR-200c-expressing clones showed a significantly reduced wound-closing efficiency at 48 hours.

Furthermore, real-time RT-PCR analysis revealed that the miR-200c levels expressed by the UMUC3 clones (FIG. 4C) were associated with elevated levels of E-cadherin mRNA transcripts and reduced levels of mRNA transcripts for ZEB1 and ZEB2 (FIG. 4D). These differences were also true at the protein levels, as shown for ZEB1 and ZEB2 using immunofluorescence microscopy and confocal analysis (FIG. 4E), and for E-cadherin by using western blot analysis (FIG. 4F). These changes were also associated with a reduced ERRFI-1 protein expression (FIG. 4F). Based on morphological criteria as well as biochemical and biological behavior, Applicants concluded that the UMUC3/200c clones demonstrated an MET phenotype and reduced ERRFI-1 expression.

MiR-200c Expression Reversed the Phenotype of EGFR-Resistant Cells

Expression of miR-200c in UMUC3 cells constantly but modestly reduced the mRNA transcripts of ERRFI-1 (data not shown) and ERRFI-1 protein levels (FIG. 4F). Without being bound by theory, the results suggest that an additional post-translational mechanism may be involved in ERRFI-1 down-regulation in MET clones (FIG. 4F).

By way of background, it is well documented that EGFR is subject to ligand-induced down-regulation mediated by receptor internalization and subsequent degradation by lysosome and the ubiquitin/proteasome system (27-29). Thus, it has recently been suggested that ERRFI-1 is able to bind EGFR molecules, including the trafficking EGFR molecules. It has also been suggested that ERRFI-1 becomes expressed at a time in which cells contain a sizable population of activated EGFRs that are being routed through the endosomal compartment. Accordingly, the blockade of kinase activity imposed by ERRFI-1 to trafficking EGFR molecules is expected to shift the kinase/phosphatase equilibrium in favor of phosphatases, thereby leading to a decline of phosphorylated EGFR levels and a concomitant loss of signaling competence (28).

To interrogate the location of these EGFR/ERRFI-1 complexes, we performed immunofluorescence staining and confocal microscopy studies of UMUC3 cells co-stained with antibodies specific for EGFR (FIG. 5A, green pixels) and ERRFI-1 (FIG. 5A, red pixels). The results revealed significant co-localized signals (yellow pixels) inside the cytoplasm, corresponding to high levels of EGFR trafficking, as well as on the cell membrane edges, such as ruffles. To our surprise, the distribution of EGFR molecules in the UMUC3/200c clones was very different, with most of the EGFR localized on the cell membrane, suggesting a higher rate of the surface-recycled EGFR. ERRFI-1 expression (red pixels) was also lower in UMUC3/200c cells compared to UMUC3 controls (FIG. 5A, middle and right panels, compared to left panel), which confirmed our immunoblot analysis. Overall, such results indicate that miR-200c expression made more epidermal growth factor receptors available on the cell surface of UMUC3 cells and therefore reversed the EGFR resistant phenotype.

MiR-200c Expression Affects EGFR Downstream Mitogenic Signaling.

By way of further background, feedback inhibition is an important mechanism of signaling pathway regulation and is crucial in modulating the intensity and duration of signals generated by receptors. Thus, sustained activation of the signal-regulated kinase group of MAPKinases is necessary for agonist-induced cell proliferation (30). EGF-stimulated ERK activation is often relatively transient, and in fibroblasts, EGF is a less effective mitogen than PDGF. A whole genome expression analysis on two of the UMUC3/200c clones revealed that they express moderate levels of mRNA/TGF-α, which may be responsible for autocrine loop-driven baseline EGFR activation, although the overall levels of ERRFI-1 protein are lower than the empty-vector-transfected UMUC3 cells, as previously described. Given that TGF-α uncouples internalized EGFR molecules from degradation by driving their rapid recycling to the cell surface (31, 32), ERRFI-1 may represent a means of restraining the recursive positive feedback loop generated by autocrine stimulation of the EGFR via TGF-α. Thus, a reduction of the ERRFI-1 baseline levels in the stable UMUC3/200c clones would result in higher baseline EGFR activation. Western blot analysis demonstrated that UMUC3/200c clones have indeed higher baseline EGFR autophosphorylation associated with reduced levels of ERRFI-1 as compared to UMUC3 controls (FIG. 5B). Furthermore, concentrations of C225 as low as 10 nM were sufficient to block the baseline MAPKinase activity in UMUC3/200c clones, whereas 1 μM of C225 had no effect on MAPKinase activity in UMUC3/E (FIG. 5C).

Expression of miR-200 miRNAs Enhances the Sensitivity of Bladder Cancer Cells to Anti-EGFR Treatment To determine whether morphological and biochemical changes were relevant for the mitogenic response to anti-EGFR treatment, we treated UMUC3/E and UMUC3/200c clones with increased concentrations of C225 for 36 hours and measured their proliferation index by a $^3$H-thymidine incorporation assay (FIG. 5D). The results indicate that UMUC3/200c clones were more sensitive to C225-induced growth inhibition than the UMUC3/E control clones (FIG. 5D). In particular, C225 concentrations of up to 1 μM produced cell-cycle inhibition ranging from about 40% to about 60%. In fact, such inhibition was similar or even higher in efficiency than the inhibition observed in other epithelial bladder cancer cells tested under baseline conditions (data not shown). Furthermore, we obtained the same results when we utilized other anti-EGFR agents, such as erlotinib (Tarceva) (data not shown).

The importance of ERRFI-1 in modulating the cell-cycle response to EGFR-targeted treatment was further demonstrated by specific ERRFI-1 silencing in UMUC3 and T24 cells (another E-cadherin-negative, EGFR-resistant urothelial cell). As shown in FIGS. 6A and 6B, a significant reduction of ERRFI-1 levels (FIG. 6A) was associated with a 30% cell-cycle inhibition of cells treated with 10 nM C225 (FIG. 6B). In addition, transfection of the full-length myc-tagged ERRFI-1 into sensitive, E-cadherin-positive UMUC5 cells resulted in the loss of EGFR sensitivity to relevant EGFR inhibitor concentrations (FIG. 6C). As we have previously mentioned, and according to the computer-based prediction programs, the 3'UTR of the ERRFI-1 gene contains two putative miR-200 binding sites (FIG. 6D, red rectangles).

To demonstrate that ERRFI-1 is indeed a direct target of miR-200 family members, we constructed four constructs, encompassing the 650 bp region of the 3'UTR shown in FIG. 6D. We also modified the two binding sites one by one as single mutants or both sites as double mutants. We engineered a two-base-pair site-directed mutagenesis which allowed us to identify binding differences of miR-200b/c/429 translated to modulation of the luciferase reporter's activity (FIG. 6E). Because co-transfection with either miR-200c (FIG. 6E), miR-200b or miR-429 (data not shown) and wild-type 3'UTR/ERRFI-1 significantly reduced the luciferase activity in UMUC3 and T24, and because the double mutant constructs were able to rescue this activity, we concluded that ERRFI-1 is a direct target of the miR-200 family members of miRNAs in these cells (FIG. 6E).

Because we used M1 and M2 point mutations and not deletions of the miRNA binding sites, and because the sequence complementarities between the miR-200 miRNAs and the M2 site is expanding beyond the "seed" region, we cannot conclude that M2 site is less important than the M1 site, as it may also be the result of a residual binding despite the point mutations that we introduced at this site.

To demonstrate that expression of miR-200 into EGRF-resistant T24 cells results in modulation of cell proliferation response using EGFR inhibitors, we transfected a lentiviral construct with or without the miR-200b sequence into the T24 cells to yield T24 and T24/200b clones, respectively. As shown in FIG. 6F, real-time RT-PCR analysis confirmed that the T24/200b clones had a higher level of miR-200b expression than the T24 clones with the empty lentiviral vectors. Next, we treated the cells with various concentrations of Iressa (an EGFR inhibitor) and measured the DNA replication in the cells by a $^3$H thymidine incorporation assay. We also included UMUC9 (an EGFR-sensitive cell line) in the experiments as a control. As shown in FIG. 6G, Iressa was more effective in inhibiting the DNA replication of the T24/200b clones than the T24 clones. In fact, Iressa's effect on the DNA replication of T24/200b clones was similar to its effects on the DNA replication of UMUC9 cells. In addition, miR-200b expression in T24 cells resulted in the expression of E-cadherin and an 18 fold reduction in ERRFI-1 mRNA (data not shown), suggesting a similar phenotype to the UMUC3/200c clones described above. Overall, such results further affirm that the expression of miR-200 miRNAs enhance the sensitivity of bladder cancer cells to anti-EGFR Treatment.

MiR-200c Expression in Invasive Bladder Cancers May Identify Patients That are Sensitive to EGFR Inhibitors but Drug Resistant Thirty-two patients with invasive urothelial cancers were stratified by the median miR-200c expression into two groups. Sixteen of the patients had a radical cystectomy or transurethral resection as part of the treatment. The range of miR-200c expression for the sixteen patients was 1 to 808 with a median value of 122. Ten of those sixteen patients had a miR-200c expression below the median value for the group. Of the six patients that had miR-200c expression above the median value, four are dead of disease (as of Oct. 1, 2009). In addition, as illustrated in FIG. 7, patients with a miR-200c expression less than the median had an 82% reduction in their risk for progression as compared to patients with a miR-200c expression above the median (p<0.05).

Of the thirty two patients, sixteen patients did not have a radical cystectomy as part of the treatment. The range of miR-200c expression for these sixteen patients was 14 to 1417. Six of those sixteen patients had miR-200c expression below the median value for the group. Of the ten patients with miR-200c expression above the median value, five are dead of disease and four are alive with disease (as of Oct. 1, 2009).

In regard to chemotherapy, twenty of the thirty two patients were treated. All but three of these regimens were platinum based. Eleven of the twenty patients had a miR-200c below the median value for the group. The range of miR-200c expression for the twenty patients was 1 to 1417. Of the nine patients with miR-200c expression above the median value, six are dead of disease and three are alive with disease. Ten of the twenty chemotherapy patients underwent cystectomy as a part of the overall treatment.

Overall, the above results indicate that miR-200 expression in cancer cells may be used to identify patients that are sensitive to EGFR inhibitors but drug resistant. The results also indicate that reduced miR-200 levels may improve progression free survival of patients with cancer.

Discussion

The above-described studies indicate that the that expression of the miR-200 miRNAs, in particular miR-200c and miR-200b, are sufficient to reverse the biology of bladder cancer cells with a "mesenchymal" phenotype, not only by its morphological appearance, but also by its EGFR signaling.

More particularly, above-described studies indicate that the expression of miR-200 miRNAs enhance the sensitivity of bladder cancer cells to anti-EGFR treatment. For instance, the above-described studies illustrate the enhancement of the sensitivity of EGFR-resistant mesenchymal cells to anti-EGFR treatment by the introduction of miR-200 miRNAs to the cancer cells. Importantly, the aforementioned enhancement was demonstrated for two different mesenchymal cell lines (i.e., UMUC3 and T24), by using two different members of the miR-200 family (i.e., miR-200c and miR-200b), and by using two different anti-EGFR compositions (i.e., C225 and Iressa).

The above-described studies also indicate that miR-200 miRNA levels in bladder cancer cells are directly correlated to the sensitivity of the cells to anti-EGFR treatment. In particular, the above studies revealed higher miR-200 expression patterns in EGFR-sensitive bladder cancer cells than in EGFR-resistant cells. The results also revealed increased miR-200 expression patterns in EGFR-sensitive cells after anti-EGFR treatment. However, EGFR-resistant cells did not show increased expression patterns after the same anti-EGFR treatments. Such results can be summarized in Table I below as follows:

TABLE 1

Relative miR-200 miRNA Expression Patterns in EGFR-resistant and EGFR-sensitive Bladder Cancer Cell Lines.

| Bladder Cancer Cell Line | Resistance to anti-EGFR Treatment | Relative miR-200 miRNA Expression Patterns (in the presence or absence of anti-EGFR compositions) | | | | | |
|---|---|---|---|---|---|---|---|
| | | miR-200b | miR-200c | miR-429 | miR-205 | miR-141 | E-Cadherin |
| UMUC2 | Resistant | 0 | 0 | 0 | 0 | 0 | 0 |
| UMUC3 | Resistant | 0 | 0 | 0 | 0 | 0 | 0 |
| UMUC13 | Resistant | 0 | 0 | 0 | 0 | 0 | 0 |
| KU7 | Resistant | 0 | 0 | 0 | 0 | 0 | 0 |
| UMUC6 | Sensitive | 1 | 1 | 1 | 1 | 1 | 1 |
| UMUC16 | Sensitive | 1 | 1 | 1 | 1 | 1 | 1 |
| UMUC5 | Sensitive | 1 | 1 | 1 | 1 | 1 | 1 |
| UMUC9 | Sensitive | 1 | 1 | 1 | 1 | 1 | 1 |
| 253J BV | Sensitive | 1 | 0 | 1 | 1 | 0 | 1 |

EXAMPLES

Additional details about the experimental aspects of the above-described studies are discussed in the subsections below.

Example 1

Cell lines and culture conditions. The UMUC series of urothelial carcinomas and 253J BV cells were isolated and fingerprinted and genotyped by the specimen core at the M. D. Anderson Genitourinary Specialized Program of Research Excellence in Bladder Cancer. KU7 cells were supplied by W. Benedict at M. D. Anderson. The cell lines were maintained at 37 C. in modified Eagle's minimum essential medium (MEM) supplemented with 10% fetal bovine serum, vitamins, sodium pyruvate, L-glutamine, penicillin, streptomycin, and nonessential amino acids.

Example 2

Reagents and chemicals. ImClone Systems, Inc. (New York, N.Y.) generously provided cetuximab (C225), a selective antihuman EGFR antagonist monoclonal antibody in a stock concentration of 2 mg/mL. Iressa (Astra-Zeneca) and Erlotinib/Tarceva (Genentech), which are specific EGFR kinase inhibitors have been generously provided by the manufacturer or purchased from the UT MD Anderson Pharmacy. The following antibodies were purchased from the manufacturer's list and were used for western blot analysis: EGFR (Lab Vision Corp., Fremont, Calif.); E-cadherin and P-cadherin (BD Transduction Laboratories, Lexington, Ky.); actin, and vinculin (Sigma-Aldrich Corporation, St. Louis, Mo.); ErbB receptor inhibitor-1(ERRFI-1) and EGFR (Tyr$^{1068}$; Cell Signaling Technology, Danvers, Mass.). Pre-miRNAs and antagomirs were purchased from Ambion, Inc. (Austin, Tex.). The TaqMan gene expression assays, miRNA expression assays, and ERRFI-1 were also purchased from Ambion. The short hairpin RNA (shRNA) against ERRFI-1 and non-targeting controls, as well as miR-200b RFP lentiviral system were all obtained from Open Biosystems-Thermo Scientific.

Example 3

Cell proliferation assay. Cells ($5\times10^3$) were plated in 96-well plates for 24 hours, serum-starved for 24 hours in 2% fetal calf serum supplemented with MEM, and then treated with or without EGFR inhibitors at increasing concentrations in an EGF-nonstimulated environment for 30 hours. We measured the effect of cetuximab (C225), Erlotinib (Tarceva) and Iressa on DNA synthesis by pulse-labeling cells with $^{[3H]}$ thymidine (MP Biomedicals, Santa Ana, Calif.) for 2 hours followed by lysis in 100 μL of 0.1 mol/L KOH. Cells were harvested onto fiberglass filters and incorporated tritium was quantified by β-counter.

Example 4

Wound-healing assay. UMUC3 cells ($4\times10^6$) were plated in 6-well plates for 24 to 48 hours (until they reached confluence). A diametric scratch was performed using a pipette tip followed by 2 culture media changes. Cells were photographed in several pre-marked spots as time zero. Multiple photographs were then taken at 24 and 48 hours in the same spots for comparison.

Example 5.

Plasmid construction and luciferase reporter assays. 3'UTR reporter plasmids for miR-200c were constructed via insertion of miR-200c seed sequence into the XbaI restriction site 3' to luciferase gene in the pGL3-control plasmid (Promega Corp., Madison, Wis.). An ERRFI-1 3' UTR segment of 648 bp was amplified by PCR from human cDNA and inserted into the pMIR-REPOR (Ambion) with MluI and SpeI sites. For point mutations we used the QuikChange® II Site-Directed Mutagenesis Kit (Qiagen) following manufactory's instruction. The primers for point mutations (U:C) are:

```
Mutant 1-F:
                                (SEQ ID NO: 1)
5'-ccttgtgttgctggttcctattcagtacctcctggggattgttt-3';

Mutant 1-R:
                                (SEQ ID NO: 2)
5'-aaacaatccccaggaggtactgaataggaaccagcaacacaagg-3';

Mutant 2-F:
                                (SEQ ID NO: 3)
5'-cactgatttctgcattatgtgtacagtaccggacaaaggattttattc
attttgtt-3';
and Mutant 2-R:
                                (SEQ ID NO: 4)
5'-aacaaaatgaataaaatcctttgtccggtactgtacacataatgcaga
aatcagtg-3'.
```

The sequences of the recombinant plasmids were confirmed by DNA sequencing. Reporter vector transfection was performed using Lipofectamine-2000 reagent (Invitrogen) as described previously (25). miRNA transfections were performed using 20 nmol/L Lipofectamine-2000. Plasmid transfections were carried out similarly but with 50 nM/L of reporter plasmid in 24-well plates plus 0.02 μg cytomegalovirus-renilla.

Example 6

Real-time reverse transcription-polymerase chain reaction (RT-PCR) to quantify mature, miRNAs. Total RNA was extracted using a Mirvana extraction reverse transcription kit (Applied Biosystems) and 10 ng total RNA along with miR-specific primer miRNA were used for expression analysis. cDNA was synthesized using Taqman miRNA specific kit (Ambion-Applied Biosystems).

Example 7

Immunoblots. Cells were treated with cetuximab (C225) for 3 hours, harvested at approximately 75% to 80%, and lysed. Protein concentration was assayed using the Bio-Rad protein assay reagent (Bio-Rad Laboratories, Hercules, Calif.). To prepare cell extracts, cells were washed 3 times with phosphate-buffered saline, and then lysed with RIPA buffer [50 mM Tris-HCl, pH 7.5; 150 mM NaCl; 0.5% NP-40; 0.1% sodium dodecyl sulfate; 0.1% sodium deoxycholate; protease inhibitor cocktail (Roche Applied Science, Indianapolis, Ind.); and 1 mM sodium ortho-vanadate] for 20 minutes on ice. To measure the activity (phosphorylation) of EGFR, we used an anti-Tyr-1068-specific antibody (Cell Signaling Technology) raised against the kinase, which measures the level of autophosphorylated EGFR. Western blot analyses were performed as previously described (25). Antibodies anti-phosphorylated p42/44 MAPKinase and pp42/44 were purchased from Cell Signaling Technology. All chemicals were purchased from Sigma Immunochemicals.

Example 8

Indirect immunofluorescence staining. Cellular localization of EGFR and ERRFI1 was determined using indirect immunofluorescence as previously described (24). Briefly, cells grown on glass coverslips were fixed (without permeabilization) in 3.7% paraformaldehyde at room temperature for 10 minutes and then extracted with ice-cold acetone. Cells were treated with or without anti-EGFR (LabVision, Inc.) and ERRFI-1 antibodies (Cell Signaling Technology) and then treated with Alexa-488-labeled goat anti-rabbit and Alexa-546-labeled goat anti-mouse secondary antibodies (Molecular Probes, Inc., Eugene, Oreg.). Confocal analysis was carried out using a Zeiss laser-scanning confocal microscope and established methods involving processing of the same section for each detector (2 excitations corresponding to 546 and 488). Co-localization of the 2 proteins (EGFR and ERRFI-1) was indicated by the presence of yellow color as a result of overlapping red and green pixels.

Example 9

RNA isolation, microarray platform, and statistics. All transcriptome data were generated from duplicates of the cell lines. Cells were plated and total RNA was isolated independently using Trizol reagent (Roche), followed by clean-up with RNeasy® Mini kit (Qiagen, Valencia, Calif.). RNA was used for the synthesis of biotin-labeled cRNA, which was prepared using the Illumina RNA amplification kit (Ambion, Inc.). Briefly, 500 ng of total RNA from each specimen was converted to cDNA then to cRNA by in vitro transcription. After purification, 1.5 μg of cRNA was fragmented and hybridized to Illumina human-6 v 2 (Illumina, Inc., San Diego, Calif.) chip. After being washed, the slides were scanned with Bead Station 500X (Illumina, Inc.), and the signal intensities were quantified with Bead Studio (Illumina, Inc.). Quantile normalization was used to normalize the data.

Example 10

Statistics. Each experiment was performed at least twice and at least one duplicate. MiRNA data normalization was performed by VSN. All calculations including statistical analysis were performed by one-way or multi-way ANOVA. miRNA target prediction and associated mRNA pathway analysis were performed using Ingenuity Pathway Analysis and TargetScan (www.targetscan.org).

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

CITED REFERENCES

1. Dinney C P, McConkey D J, Millikan R E, Wu X, Bar-Eli M, Adam L, Kamat A M, Siefker-Radtke A O, Tuziak T, Sabichi A L, Grossman H B, Benedict W F, Czerniak B. Focus on bladder cancer. Cancer Cell. 2004 August; 6(2):111-6. Review.
2. Dreicer R. Advanced bladder cancer: So many drugs, so little progress: what's wrong with this picture? Cancer. 2008 Jul. 9.
3. Zhang X, Atala A, Godbey W T. Expression-targeted gene therapy for the treatment of transitional cell carcinoma. Cancer Gene Ther. 2008 Mar. 7.
4. Agarwal P K, Black P C, McConkey D J, Dinney C P. Emerging drugs for targeted therapy of bladder cancer. Expert Opin Emerg Drugs. 2007 September; 12(3):435-48. Review.
5. Blaveri E, Brewer J L, Roydasgupta R, Fridlyand J, DeVries S, Koppie T, Pejavar S, Mehta K, Carroll P, Simko J P, Waldman F M. Bladder cancer stage and outcome by array-based comparative genomic hybridization. Clin Cancer Res. 2005 Oct. 1; 11(19 Pt 1):7012-22.
6. Haber D A, Bell D W, Sordella R, Kwak E L, Godin-Heymann N, Sharma S V, Lynch T J, Settleman J. Molecular targeted therapy of lung cancer: EGFR mutations and response to EGFR inhibitors. Cold Spring Harb Symp Quant Biol. 2005; 70:419-26. Review.
7. Blehm K N, Spiess P E, Bondaruk J E, Dujka M E, Villares G J, Zhao Y J, Bogler O, Aldape K D, Grossman H B, Adam L, McConkey D J, Czerniak B A, Dinney C P, Bar-Eli M. Mutations within the kinase domain and truncations of the epidermal growth factor receptor are rare events in bladder cancer: implications for therapy. Clin Cancer Res. 2006 Aug. 1; 12(15):4671-7.
8. Yauch R L, Januario T, Eberhard D A, Cavet G, Zhu W, Fu L, Pham T Q, Soriano R, Stinson J, Seshagiri S, Modrusan Z, Lin C Y, O'Neill V, Amler L C. Epithelial versus mesenchymal phenotype determines in vitro sensitivity and predicts clinical activity of erlotinib in lung cancer patients. Clin Cancer Res. 2005 Dec. 15; 11(24 Pt 1):8686-98.
9. Miyanaga A, Gemma A, Ando M, Kosaihira S, Noro R, Minegishi Y, Kataoka K, Nara M, Okano T, Miyazawa H, Tanaka T, Yoshimura A, Kobayashi K, Iwanami H, Hagiwara K, Tsuboi E, Kudoh S. E-cadherin expression and epidermal growth factor receptor mutation status predict outcome in non-small cell lung cancer patients treated with gefitinib. Oncol Rep. 2008 February; 19(2):377-83.
10. Shrader M, Pino M S, Brown G, Black P, Adam L, Bar-Eli M, Dinney C P, McConkey D J. Molecular correlates of gefitinib responsiveness in human bladder cancer cells. Mol Cancer Ther. 2007 January; 6(1):277-85
11. Witta S E, Gemmill R M, Hirsch F R, Coldren C D, Hedman K, Ravdel L, Helfrich B, Dziadziuszko R, Chan D C, Sugita M, Chan Z, Baron A, Franklin W, Drabkin H A, Girard L, Gazdar A F, Minna J D, Bunn P A Jr. Restoring E-cadherin expression increases sensitivity to epidermal growth factor receptor inhibitors in lung cancer cell lines. Cancer Res. 2006 Jan. 15; 66(2):944-50.
12. Black P C, Brown G A, Inamoto T, Shrader M, Arora A, Siefker-Radtke A O, Adam L, Theodorescu D, Wu X, Munsell M F, Bar-Eli M, McConkey D J, Dinney C P. Sensitivity to epidermal growth factor receptor inhibitor requires E-cadherin expression in urothelial carcinoma cells. Clin Cancer Res. 2008 Mar. 1; 14(5):1478-86.
13. Thomson S, Buck E, Petti F, Griffin G, Brown E, Ramnarine N, Iwata K K, Gibson N, Haley J D. Epithelial to mesenchymal transition is a determinant of sensitivity of non-small-cell lung carcinoma cell lines and xenografts to epidermal growth factor receptor inhibition. Cancer Res. 2005 Oct. 15; 65(20):9455-62.
14. Mani S A, Guo W, Liao M J, Eaton E N, Ayyanan A, Zhou A Y, Brooks M, Reinhard F, Zhang C C, Shipitsin M, Campbell L L, Polyak K, Brisken C, Yang J, Weinberg R A. The epithelial-mesenchymal transition generates cells with properties of stem cells. Cell. 2008 May 16; 133(4): 704-15.
15. Pettitt J. The cadherin superfamily. WormBook. 2005 Dec. 29: 1-9. Review.
16. Hurteau G J, Carlson J A, Spivack S D, Brock G J. Overexpression of the microRNA hsa-miR-200c leads to reduced expression of transcription factor 8 and increased expression of E-cadherin. Cancer Res. 2007 Sep. 1; 67(17): 7972-6.
17. Gregory P A, Bert A G, Paterson E L, Barry S C, Tsykin A, Farshid G, Vadas M A, Khew-Goodall Y, Goodall G J. The miR-200 family and miR-205 regulate epithelial to mesenchymal transition by targeting ZEB1 and SIP1. Nat Cell Biol. 2008 May; 10(5):593-601.
18. Korpal M, Lee E S, Hu G, Kang Y. The miR-200 family inhibits epithelial-mesenchymal transition and cancer cell migration by direct targeting of E-cadherin transcriptional repressors ZEB1 and ZEB2. J Biol Chem. 2008 May 30; 283(22):14910-4.
19. Park S M, Gaur A B, Lengyel E, Peter M E. The miR-200 family determines the epithelial phenotype of cancer cells by targeting the E-cadherin repressors ZEB1 and ZEB2. Genes Dev. 2008 Apr. 1; 22(7):894-907.
20. Gregory R I, Chendrimada T P, Cooch N, Shiekhattar R. Human RISC couples microRNA biogenesis and posttranscriptional gene silencing. Cell. 2005 Nov. 18; 123(4):631-40.
21. Gregory R I, Chendrimada T P, Shiekhattar R. MicroRNA biogenesis: isolation and characterization of the microprocessor complex. Methods Mol Biol. 2006; 342:33-47. Review.
22. Calin, G. A., and Croce, C. M. MicroRNA signatures in human cancers. Nature Reviews Cancer 2006; 6:857-66 Review.
23. Esquela-Kerscher A, Slack F J. Oncomirs—microRNAs with a role in cancer. Nat Rev Cancer. 2006 April; 6(4): 259-69.
24. Ma L, Teruya-Feldstein J, Weinberg R A. Tumour invasion and metastasis initiated by microRNA-10b in breast cancer. Nature. 2007 Oct. 11; 449(7163):682-8.
25. Kassouf W, Dinney C P, Brown G, McConkey D J, Diehl A J, Bar-Eli M, Adam L. Uncoupling between epidermal growth factor receptor and downstream signals defines resistance to the antiproliferative effect of Gefitinib in bladder cancer cells. Cancer Res. 2005 Nov. 15; 65(22): 10524-35.
26. Dinney C P, Fishbeck R, Singh R K, Eve B, Pathak S, Brown N, Xie B, Fan D, Bucana C D, Fidler I J, et al. Isolation and characterization of metastatic variants from human transitional cell carcinoma passaged by orthotopic implantation in athymic nude mice. J Urol. 1995 October; 154(4): 1532-8.
27. Wiley H S. Trafficking of the ErbB receptors and its influence on signaling. Exp Cell Res. 2003 Mar. 10; 284 (1):78-88.
28. Sweeney C, Carraway K L 3rd. Negative regulation of ErbB family receptor tyrosine kinases. Br J Cancer. 2004 Jan. 26; 90(2):289-93
29. Schulze W X, Deng L, Mann M. Phosphotyrosine interactome of the ErbB-receptor kinase family. Mol Syst Biol. 2005; 1:2005.0008
30. Brunet A, Roux D, Lenormand P, Dowd S, Keyse S, Pouysségur J. Nuclear translocation of p42/p44 mitogen-activated protein kinase is required for growth factor-induced gene expression and cell cycle entry. EMBO J. 1999 Feb. 1; 18(3):664-74.
31. Lenferink A E, Pinkas-Kramarski R, van de Poll M L, van Vugt M J, Klapper L N, Tzahar E, Waterman H, Sela M, van Zoelen E J, Yarden Y. Differential endocytic routing of homo- and hetero-dimeric ErbB tyrosine kinases confers signaling superiority to receptor heterodimers. EMBO J. 1998 Jun. 15; 17(12):3385-97.
32. Longva K E, Blystad F D, Stang E, Larsen A M, Johannessen L E, Madshus I H. Ubiquitination and proteasomal activity is required for transport of the EGF receptor to inner membranes of multivesicular bodies. J Cell Biol. 2002 Mar. 4; 156(5):843-54.
33. Fiorini M, Ballarò C, Sala G, Falcone G, Alemà S, Segatto O. Expression of RALT, a feedback inhibitor of ErbB receptors, is subjected to an integrated transcriptional and post-translational control. Oncogene. 2002 Sep. 19; 21(42):6530-9.
34. Lafont J E, Talma S, Hopfgarten C, Murphy C L. Hypoxia promotes the differentiated human articular chondrocyte phenotype through SOX9-dependent and -independent pathways. J Biol Chem. 2008 Feb. 22; 283(8):4778-86.
35. Zhang Y W, Vande Woude G F. Mig-6, signal transduction, stress response and cancer. Cell Cycle. 2007 Mar. 1; 6(5):507-13.

36. Makkinje A, Quinn D A, Chen A, Cadilla C L, Force T, Bonventre J V, Kyriakis J M. Gene 33/Mig-6, a transcriptionally inducible adapter protein that binds GTP-Cdc42 and activates SAPK/JNK. A potential marker transcript for chronic pathologic conditions, such as diabetic nephropathy. Possible role in the response to persistent stress. J Biol Chem. 2000 Jun. 9; 275(23):17838-47.

37. Anastasi S, Baietti M F, Frosi Y, Alemà S, Segatto O. The evolutionarily conserved EBR module of RALT/MIG6 mediates suppression of the EGFR catalytic activity. Oncogene. 2007 Dec. 13; 26(57):7833-46.

38. Anastasi S, Fiorentino L, Fiorini M, Fraioli R, Sala G, Castellani L, Alemà S, Alimandi M, Segatto O. Feedback inhibition by RALT controls signal output by the ErbB network. Oncogene. 2003 Jul. 3; 22(27):4221-34.

39. Fiorentino L, Pertica C, Fiorini M, Talora C, Crescenzi M, Castellani L, Alemà S, Benedetti P, Segatto O. Inhibition of ErbB-2 mitogenic and transforming activity by RALT, a mitogen-induced signal transducer which binds to the ErbB-2 kinase domain. Mol Cell Biol. 2000 October; 20(20):7735-50.

40. Zhang X, Pickin K A, Bose R, Jura N, Cole P A, Kuriyan J. Inhibition of the EGF receptor by binding of MIG6 to an activating kinase domain interface. Nature. 2007 Nov. 29; 450(7170):741-4.

41. Khambata-Ford S, Garrett C R, Meropol N J, Basik M, Harbison C T, Wu S, Wong T W, Huang X, Takimoto C H, Godwin A K, Tan B R, Krishnamurthi S S, Burris H A 3rd, Poplin E A, Hidalgo M, Baselga J, Clark E A, Mauro D J. Expression of epiregulin and amphiregulin and K-ras mutation status predict disease control in metastatic colorectal cancer patients treated with cetuximab. J Clin Oncol. 2007 Aug. 1; 25(22):3230-7.

42. Wu W, O'Reilly M S, Langley R R, Tsan R Z, Baker C H, Bekele N, Tang X M, Onn A, Fidler I J, Herbst R S. Expression of epidermal growth factor (EGF)/transforming growth factor-alpha by human lung cancer cells determines their response to EGF receptor tyrosine kinase inhibition in the lungs of mice. Mol Cancer Ther. 2007 October; 6(10):2652-63.

43. Pece S, Gutkind J S. Signaling from E-cadherins to the MAPK pathway by the recruitment and activation of epidermal growth factor receptors upon cell-cell contact formation. J Biol Chem. 2000 Dec. 29; 275(52):41227-33.

What is claimed is:

1. A method of treating a patient having cancer that is resistant to EGFR treatment using anti-EGFR treatment, said method comprising the steps of administering to cells of said cancer an amount of a miR-200 miRNA that is effective to render said cancer sensitive to anti-EGFR treatment; and treating said patient with an anti-EGFR composition.

2. The method of claim 1, wherein said miR-200 miRNA is selected from the group consisting of miR-200b and miR-200c.

3. The method of claim 1, wherein said miR-200 miRNA is administered to said cancer cells by transfecting said cancer cells with said miR-200 miRNA.

4. The method of claim 3, wherein said miR-200 miRNA is comprised in a nanovector.

5. The method of claim 3, wherein said transfecting comprises lipofection.

6. The method of claim 1, wherein said miR-200 miRNA is administered introduced to said cancer cells by a targeted delivery method which comprises the use of a targeting moiety that binds to said cancer cells.

7. The method of claim 6, wherein said targeting moiety is an antibody.

8. The method of claim 6, wherein the targeting moiety is an aptamer.

9. The method of claim 6, wherein the targeting moiety is a dendrimer.

10. The method of claim 1, wherein said miR-200 miRNA is administered to said cancer cells cancer by means of vector that encodes a nucleotide sequence for said miR-200 microRNA.

11. The method of claim 1, wherein said anti-EGFR treatment comprises treatment of said cancer cells with an anti-EGFR antibody or a small molecule EGFR tyrosine kinase inhibitor.

12. The method of claim 1, wherein said patient has a cancer that is selected from the group consisting of bladder cancer, breast cancer, pancreatic cancer, lung cancer, and colon cancer.

13. A method of treating cancer using anti-EGFR treatment, said method comprising measuring the level of a miR-200 miRNA in said cancer cells; administering a miR-200 miRNA to said cancer cells to enhance the sensitivity of said cancer cells to anti-EGFR treatment; and treating said cancer cells with an anti-EGFR composition.

14. The method of claim 13, wherein said measuring step comprises real-time RT-PCR analysis of the RNA of said cancer cells.

15. The method of claim 13, wherein said measuring step comprises a measurement of a miR-200 miRNA level in a patient's blood or urine sample.

16. The method of claim 13, wherein said miR-200 miRNA is selected from the group consisting of miR-200b and miR-200c.

* * * * *

```
                          SEQUENCE LISTING

<160> NUMBER OF SEQ ID NOS: 4

<210> SEQ ID NO 1
<211> LENGTH: 44
<212> TYPE: DNA
<213> ORGANISM: Artificial Sequence
<220> FEATURE:
<223> OTHER INFORMATION: Synthetic primer

<400> SEQUENCE: 1
ccttgtgttg ctggttccta ttcagtacct cctggggatt gttt            44

<210> SEQ ID NO 2
<211> LENGTH: 44
<212> TYPE: DNA
<213> ORGANISM: Artificial Sequence
<220> FEATURE:
<223> OTHER INFORMATION: Synthetic primer

<400> SEQUENCE: 2
aaacaatccc caggaggtac tgaataggaa ccagcaacac aagg            44

<210> SEQ ID NO 3
<211> LENGTH: 56
<212> TYPE: DNA
<213> ORGANISM: Artificial Sequence
<220> FEATURE:
<223> OTHER INFORMATION: Synthetic primer

<400> SEQUENCE: 3
cactgatttc tgcattatgt gtacagtacc ggacaaagga ttttattcat tttgtt      56

<210> SEQ ID NO 4
<211> LENGTH: 56
<212> TYPE: DNA
<213> ORGANISM: Artificial Sequence
<220> FEATURE:
<223> OTHER INFORMATION: Synthetic primer

<400> SEQUENCE: 4
aacaaaatga ataaaatcct ttgtccggta ctgtacacat aatgcagaaa tcagtg      56
```